US012630558B2

(12) United States Patent
Little et al.

(10) Patent No.: US 12,630,558 B2
(45) Date of Patent: May 19, 2026

(54) PYRIDINE DERIVATIVES AS MODULATORS OF SORTILIN ACTIVITY

(71) Applicant: Vesper Bio ApS, Copenhagen (DK)

(72) Inventors: Paul Brian Little, Copenhagen (DK); Manuel Javier Cases-Thomas, Copenhagen (DK); Mads Fuglsang Kjølby, Copenhagen (DK); Anders Nykjær, Copenhagen (DK)

(73) Assignee: VESPER BIO APS, Copenhagen (DK)

( * ) Notice: Subject to any disclaimer, the term of this patent is extended or adjusted under 35 U.S.C. 154(b) by 413 days.

(21) Appl. No.: 18/273,225

(22) PCT Filed: Jan. 20, 2022

(86) PCT No.: PCT/EP2022/051282
§ 371 (c)(1),
(2) Date: Jul. 19, 2023

(87) PCT Pub. No.: WO2022/157271
PCT Pub. Date: Jul. 28, 2022

(65) Prior Publication Data

US 2024/0132514 A1 Apr. 25, 2024

(30) Foreign Application Priority Data

Jan. 20, 2021 (EP) .................................... 21152638

(51) Int. Cl.

| | |
|---|---|
| *C07D 471/04* | (2006.01) |
| *C07D 213/75* | (2006.01) |
| *C07D 491/052* | (2006.01) |
| *C07D 491/056* | (2006.01) |

(52) U.S. Cl.
CPC ....... *C07D 491/056* (2013.01); *C07D 213/75* (2013.01); *C07D 471/04* (2013.01); *C07D 491/052* (2013.01)

(58) Field of Classification Search
CPC .................................................. C07D 491/056
USPC .......................................................... 514/302
See application file for complete search history.

(56) References Cited

U.S. PATENT DOCUMENTS 9,464,065 B2 * 10/2016 Schultz .............. A61K 38/1825

FOREIGN PATENT DOCUMENTS

| | | |
|---|---|---|
| WO | 2009132656 A2 | 11/2009 |
| WO | 2014114779 A1 | 7/2014 |

OTHER PUBLICATIONS

International Search Report for corresponding International Application No. PCT/EP2022/051282, dated Apr. 13, 2022.
Rhost, Sara, et al. "Sortilin inhibition limits secretion-induced progranulin-dependent breast cancer progression and cancer stem cell expansion." Breast Cancer Research 20 (2018): 1-15.

* cited by examiner

*Primary Examiner* — Niloofar Rahmani
(74) *Attorney, Agent, or Firm* — Barnes & Thornburg; Lisa D. Fazzino

(57) ABSTRACT

The present invention relates to compounds of formula (I), which are modulators of sortilin activity. The invention also relates to pharmaceutical compositions comprising these compounds and to the use of these compounds in the treatment or prevention of medical conditions where modulation of sortilin activity is beneficial.

(I)

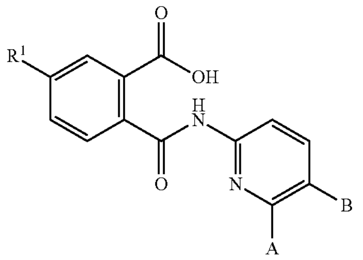

10 Claims, 1 Drawing Sheet

Specification includes a Sequence Listing.

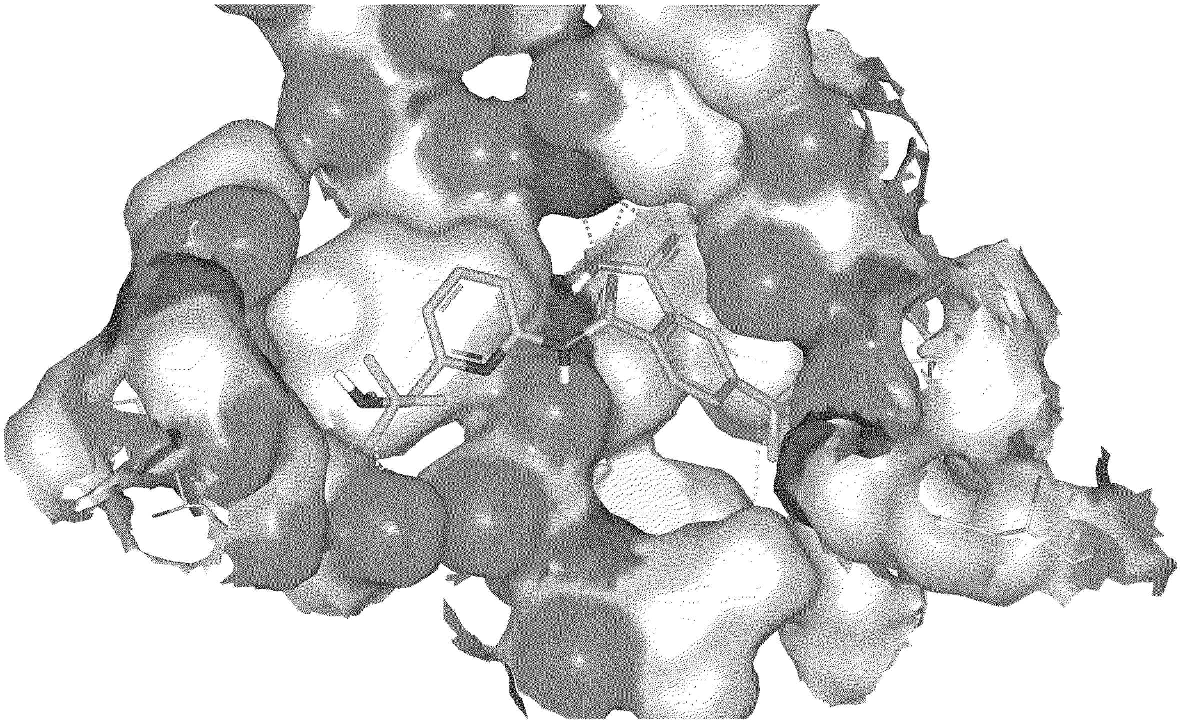

PYRIDINE DERIVATIVES AS MODULATORS OF SORTILIN ACTIVITY

RELATED APPLICATIONS

This application is a National Stage application of International Application No. PCT/EP2022/051282, filed Jan. 20, 2022 which claims priority under 35 U.S.C. § 119 to European Patent Application No. 21152638.9, filed Jan. 20, 2021.

SEQUENCE LISTING

The Sequence Listing associated with this application is provided in TXT format in lieu of paper copy and is hereby incorporated by reference into the specification. The name of the TXT file containing the Sequence Listing is "87764-392371Sequence List_ST25.txt". The TXT file is 19.9 KB, was created on Jan. 20, 2022, and was submitted electronically with the filing of the International Application PCT/EP2022/051282.

FIELD OF THE INVENTION

The present invention relates to compounds of formula (I), which are modulators of sortilin activity. The invention also relates to pharmaceutical compositions comprising these compounds and to the use of these compounds in the treatment or prevention of medical conditions where modulation of sortilin activity is beneficial. Such medical conditions include mental diseases, diabetes, diabetes-related conditions and hearing loss.

BACKGROUND

Sortilin (encoded by SORT1) is a type 1 membrane receptor in the vacuolar protein sorting 10 protein (VPS10P) family of sorting receptors, and is abundantly expressed in the central nervous system, the inner ear, and in some peripheral tissues involved in metabolic control[1,2,3,4]. Sortilin has an amino acid sequence according to SEQ ID NO: 1 and comprises a signal peptide, a propeptide, the Vps10p domain, a 10cc domain (10CCa+10CCb), a transmembrane domain and a large cytoplasmic tail. The luminal domain of sortilin has 6 potential N-linked glycosylation sites, whilst the cytoplasmic tail enables for the recruitment of various adapter proteins.

Sortilin binds to a vast number of ligands and membrane receptors and as a result engages in functions known to be important in cellular signaling and sorting. For example, sortilin is involved in signaling by proneurotrophins: the proforms of nerve growth factor (proNGF), brain derived neurotrophic factor (proBDNF), and neurotrophin-3 (proNT3), respectively. In complex with the protein p75NTR (p75 neurotrophin receptor), sortilin has been reported to form the receptor for proneurotrophin-mediated apoptotic effects leading to degeneration and cell death in cellular and animal models[5,6,7].

Previous work has suggested a role for sortilin in cellular sorting and signalling associated with diseases such as diabetes and obesity (Huang et al 2013 Mol Biol Cell October;24(19):3115-22). Sortilin facilitates translocation of GLUT4 to the plasma membrane and rescues it from degradation in the lysosomes (Pan et al Mol Biol Cell. 2017 June 15;28(12):1667-1675). Sortilin levels have been shown to be modulated by the level of inflammation associated with these diseases. The pro-inflammatory cytokine, TNFα, reduces both mRNA levels and protein levels of sortilin in cultured mouse and human adipocytes, as well as in vivo when injected into mice (Kaddai et al. Diabetologia 52: 932-40, 2009). Sortilin can also influence cytokine secretion: targeting sortilin in immune cells has been proposed to attenuate inflammation and reduce atherosclerosis disease progression (Mortensen et al. J Clin Invest 124(12):5317-22, 2014). Additionally, US 2016/0331746 describes various scaffolds of small molecules capable of binding to the active site of sortilin. Sortilin is involved in the regulation of glucose uptake (Shi & Kandror. Developmental Cell 9:99-108, 2005) and the development of lipid disorder diseases (Gao et al. DNA and Cell Biology 36(12):1050-61, 2017).

Further, plasma sortilin levels have been reported to be a potential biomarker for identifying patients with either coronary heart disease or diabetes mellitus (Oh et al. Cardiovascular Diabetology 16:92, 2017). Patients that showed increased sortilin levels within their plasma, and therefore identifiable as suffering from the above conditions, also displayed enhanced glucose levels suggesting sortilin as a therapeutic target for treating these conditions.

In view of the above, there is an unmet need for new compounds that may be used in the treatment and prevention of medical conditions in which modulation of sortilin is beneficial, such as neurodegenerative disorders, cancer, pain, diabetes mellitus, diabetic retinopathy, cardiovascular disease, hereditary eye conditions and hearing loss.

DESCRIPTION OF THE FIGURES

FIG. 1 depicts a virtual binding representation showing the interaction between the compound of example 23 and sortilin.

DISCLOSURE OF THE INVENTION

In a first aspect, the present invention provides a compound of formula (I)

(I)

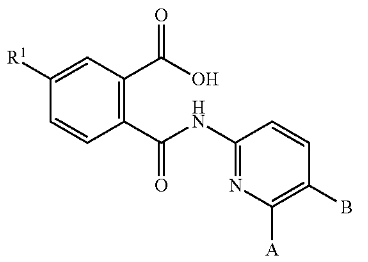

or a pharmaceutically acceptable salt, solvate, hydrate, tautomer, optical isomer, N-oxide, and/or prodrug thereof, wherein A is selected from the group consisting of H, —OH, $C_1$-$C_4$ hydroxyalkyl, $C_2$-$C_4$ alkyl, $C_1$-$C_4$ haloalkyl, $C_1$-$C_4$ alkoxy, $C_1$-$C_4$ haloalkoxy and $C_1$-$C_4$ aminoalkyl;

B is selected from the group consisting of H, —OH, $C_1$-$C_4$ alkyl, $C_1$-$C_4$ haloalkyl, $C_1$-$C_4$ alkoxy and $C_1$-$C_4$ haloalkoxy; or A and B may be taken together with the carbon atom to which they are respectively attached to form a 5- to 7-membered monocyclic heterocyclic ring that is optionally substituted with one or more substituents independently selected from —OH, $C_1$-$C_4$ alkyl, $C_1$-$C_4$ haloalkyl and $C_1$-$C_4$ alkoxy and $C_1$-$C_4$ haloalkoxy; and $R^1$ is selected from the group consisting of halo, $C_1$-$C_6$ alkyl, $C_2$-$C_6$ alkenyl, halo $C_1$-$C_6$ alkyl, and halo $C_2$-$C_6$ alkenyl.

It has been surprisingly found that compounds of formula (I) inhibit or antagonise sortilin and therefore may be useful in conditions where sortilin inhibition is beneficial. Such conditions include neurodegenerative disorders, cancer, pain, diabetes mellitus, diabetic retinopathy, cardiovascular disease, hereditary eye conditions and hearing loss.

As used herein, the term "sortilin" may refer to full length sortilin (also referred to as immature sortilin), comprising a signal peptide, a propeptide, a Vps10p domain, a 1000 domain, a transmembrane domain and a large cytoplasmic tail, having an amino acid sequence according to SEQ ID NO: 1 or SEQ ID NO: 2, or it may refer to mature sortilin, comprising a Vps10p domain, a 1000 domain, a transmembrane domain and a large cytoplasmic tail, having an amino acid sequence according to SEQ ID NO: 3, ora naturally occurring fragment, homologue or variant thereof. The term "sortilin" or "sortilin molecule" are used interchangeably herein. It is understood that the sortilin is capable of interacting with a pro-neurotrophin molecule to form a sortilin/pro-neurotrophin complex. This sortilin/pro-neurotrophin complex may or may not be capable of interacting with a p75NTR molecule to form a trimeric complex comprising sortilin, pro-neurotrophin and p75NTR. It is understood that this trimeric complex may be responsible for adverse biological responses, such as stimulating apoptosis in retinal and ganglion cells, and controlling growth cone retraction of projecting axons.

As used herein, the term "pro-neurotrophin" refers to the larger precursors of neurotrophins, which undergo proteolytic cleavage to yield the mature form of the neurotrophin. Neurotrophins are a family of proteins that induce the survival, development and function of neurons, and are commonly referred to as growth factors. Pro-neurotrophins are biologically active and have distinct roles compared to their neurotrophin counterparts, such as induction of apoptosis. Examples of pro-neurotrophins include proNGF, proBDNF, proNT3 and proNT4. Pro-neurotrophins may also control synaptic plasticity. Whereas mature neurotrophins induce synaptic strength, in their proforms they may weaken synapses, The compounds of the invention may be sortilin inhibitors or antagonists. As used herein, the term "sortilin antagonist" refers to a substance that interferes with, blocks, or otherwise attenuates the effect of, a sortilin protein binding to a pro-neurotrophin (e.g., proNGF, proNT3, proBDNF) and preventing the formation of the trimeric complex between sortilin, p75NTR and the pro-neurotrophin. The term "sortilin antagonist" also includes a substance or agent that interferes with the formation of a high affinity trimeric complex. In the latter scenario, it is recognised that a trimeric complex may be formed in that sortilin can bind to p75NTR (but not proNGF) and p75NTR can simultaneously bind the NGF domain of proNGF. However, the resulting trimeric complex may be of lower affinity for its receptor and as a result have significantly reduced capacity to stimulate apoptosis via the mechanism described above. Skeldal et al (J. Biol. Chem. 2012 December 21;287(52):43798-809) demonstrated that the apoptotic function of the trimeric complex is abolished when sortilin is devoid in its intracellular domain. The term "sortilin antagonist" also includes a substance or agent that interferes with, blocks, or otherwise attenuates the effect of, a sortilin protein interacting with p75NTR. This interaction may be completely prevented, in which case the trimeric complex is prevented from forming, or only partially prevented, in which case the trimeric complex may be formed but may have reduced biological potency. Skeldal et al showed that complex formation between sortilin and p75NTR relies on contact points in the extracellular domains of the receptors and that the interaction critically depends on an extracellular juxtamembrane 23-amino acid sequence of p75NTR. Thus, the sortilin antagonist may interfere with this 23-amino acid sequence or proximal sequences in the molecules.

In the first aspect of the invention, it is preferred that R 1 is selected from the group consisting of halo, $C_1$-$C_4$ alkyl and halo $C_1$-$C_4$ alkyl. It is more preferred that $R^1$ is fluoro $C_1$-$C_4$ alkyl.

In a preferred aspect of the invention, $R^1$ is selected from the group consisting of $CF_3$ and t-butyl.

In another preferred aspect of the invention, A is selected from the group consisting of $C_1$-$C_4$ hydroxyalkyl and $C_1$-$C_4$ alkoxy.

It is also preferred that B is selected from the group consisting of H, $C_1$-$C_4$ haloalkyl and $C_1$-$C_4$ alkyl. It is more preferred that B is H.

In another preferred aspect of the invention, A and B are taken together with the carbon atom to which they are respectively attached to form a 5- to 7-membered monocyclic heterocyclic ring that is optionally substituted with one or more substituents independently selected from $C_1$-$C_4$ alkyl and $C_1$-$C_4$ haloalkyl.

It is more preferred that A and B are taken together with the carbon atom to which they are respectively attached to form a 6-membered monocyclic heterocyclic ring that is optionally substituted with one or more substituents independently selected from $C_1$-$C_4$ alkyl and $C_1$-$C_4$ haloalkyl.

It is more preferred that the 6-membered monocyclic heterocyclic ring is unsubstituted.

It is even more preferred that the 6-membered monocyclic heterocyclic ring comprises an oxygen atom.

In even more preferred embodiments, the compound of formula (I) is a compound of formula (Ia)

(Ia)

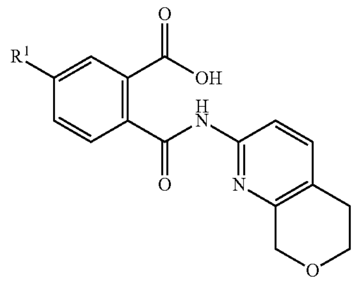

wherein $R^1$ is selected from the group consisting of halo, $C_1$-$C_4$ alkyl and halo $C_1$-$C_4$ alkyl. It is more preferred that $R^1$ is fluoro $C_1$-$C_4$ alkyl. It is most preferred that $R^1$ is selected from the group consisting of $CF_3$ and t-butyl.

In a particularly preferred embodiment of the invention:

A is selected from the group consisting of $C_1$-$C_4$ hydroxyalkyl and $C_1$-$C_4$ alkoxy;

B is selected from the group consisting of H, $C_1$-$C_4$ haloalkyl and $C_1$-$C_4$ alkyl; or A and B are taken together with the carbon atom to which they are respectively attached to form a 6-membered monocyclic heterocyclic ring that is optionally substituted with one or more substituents independently selected from $C_1$-$C_4$ alkyl and $C_1$-$C_4$ haloalkyl; and $R^1$ is selected from the group consisting of halo, $C_1$-$C_4$ alkyl and halo $C_1$-$C_4$ alkyl.

In another preferred embodiment of the invention:

A is selected from the group consisting of $C_1$-$C_4$ hydroxyalkyl and $C_1$-$C_4$ alkoxy;

B is H; or

A and B are taken together with the carbon atom to which they are respectively attached to form an unsubstituted 6-membered monocyclic heterocyclic ring; and $R^1$ is selected from the group consisting of $CF_3$ and t-butyl.

Particular compounds of the invention are those listed below.

2-({5H,6H,8H-pyrano[3,4-b]pyridin-2-yl}carbamoyl)-5-(trifluoromethyl)benzoic acid;

2-{[6-(hydroxymethyl)pyridin-2-yl]carbamoyl}-5-(trifluoromethyl)benzoic acid;

5-tert-butyl-2-{[6-(hydroxymethyl)pyridin-2-yl]carbamoyl}benzoic acid;

(RAC) 2-{[6-(1-hydroxyethyl)pyridin-2-yl]carbamoyl}-5-(trifluoromethyl)benzoic acid;

2-({6-[(1S)-1-hydroxyethyl]pyridin-2-yl}carbamoyl)-5-(trifluoromethyl)benzoic acid;

2-({6-[(1R)-1-hydroxyethyl]pyridin-2-yl}carbamoyl)-5-(trifluoromethyl)benzoic acid;

2-{[6-(2-hydroxypropan-2-yl)pyridin-2-yl]carbamoyl}-5-(trifluoromethyl)benzoic acid;

2-{[6-(2-hydroxyethyl)pyridin-2-yl]carbamoyl}-5-(trifluoromethyl)benzoic acid;

(RAC) 5-tert-butyl-2-{[6-(1-hydroxyethyppyridin-2-yl]carbamoyl}benzoic acid;

5-tert-butyl-2-({6-[(1R)-1-hydroxyethyl]pyridin-2-yl}carbamoyl)benzoic acid;

5-tert-butyl-2-({6-[(1S)-1-hydroxyethyl]pyridin-2-yl}carbamoyl)benzoic acid;

2-({2H,3H,4H-pyrano[2,3-b]pyridin-7-yl}carbamoyl)-5-(trifluoromethyl)benzoic acid;

2-({2H,3H-[1,4]dioxino[2,3-b]pyridin-6-yl}carbamoyl)-5-(trifluoromethyl)benzoic acid;

2-({5H,7H,8H-pyrano[4,3-b]pyridin-2-yl}carbamoyl)-5-(trifluoromethyl)benzoic acid;

2-[(5,6,7,8-tetrahydro-1,6-naphthyridin-2-yl)carbamoyl]-5-(trifluoromethyl)benzoic acid;

5-tert-butyl-2-({5H,6H,8H-pyrano[3,4-b]pyridin-2-yl}carbamoyl)benzoic acid;

(RAC) 2-{[6-(2,2,2-trifluoro-1 -hydroxyethyl)pyridin-2-yl]carbamoyl}-5-(trifluoromethyl)benzoic acid;

2-({6-[(1S)-2,2,2-trifluoro-1-hydroxyethyl]pyridin-2-yl}carbamoyl)-5-(trifluoromethyl)benzoic acid;

2-({6-[(1R)-2,2,2-trifluoro-1-hydroxyethyl]pyridin-2-yl}carbamoyl)-5-(trifluoromethyl)benzoic acid;

(RAC) 2-{[6-(1-amino-2,2,2-trifluoroethyl)pyridin-2-yl]carbamoyl}-5-(trifluoromethyl)benzoic acid;

2-({6-[(1R)-1-amino-2,2,2-trifluoroethyl]pyridin-2-yl}carbamoyl)-5-(trifluoromethyl)benzoic acid;

2-({6-[(1S)-1-amino-2,2,2-trifluoroethyl]pyridin-2-yl}carbamoyl)-5-(trifluoromethyl)benzoic acid;

or a pharmaceutically acceptable salt, solvate, hydrate, tautomer, optical isomer, N-oxide, and/or prodrug thereof.

The compounds of formula (I) are intended for use in the treatment or prevention of a neurodegenerative disorder, a cancer, pain, diabetes mellitus, diabetic retinopathy, cardiovascular disease, hereditary eye conditions or hearing loss. Preferably, the neurodegenerative disorder is selected from frontotemporal dementia, Alzheimer's disease, Parkinson's disease and spinal cord injury. Preferably, the hearing loss is selected from noise-induced hearing loss, ototoxicity induced hearing loss, age-induced hearing loss, idiopathic hearing loss, tinnitus and sudden hearing loss. Preferably, the cancer is selected from breast cancer, lung cancer, ovarian cancer, prostate cancer, thyroid cancer, pancreatic cancer, glioblastoma, and colorectal cancer. Preferably the cardiovascular disease is selected from atherosclerosis, cardiomyopathy, heart attack, arrhythmias, and coronary artery disease.

Thus, in an embodiment, the compounds for use according to the invention may disrupt interaction between a sortilin molecule and a pro-neurotrophin molecule, or disrupt the interaction between a sortilin molecule and a p75NTR molecule. Said sortilin molecule may be mature sortilin.

Preferably, the compounds of the present invention are sortilin inhibitors. As used herein, the term "sortilin inhibitor" refers to a compound that binds to a sortilin protein, thereby preventing it from binding to a pro-neurotrophin or a p75NTR molecule and preventing the formation of the aforementioned trimeric complex, or resulting in the formation of a trimeric complex that is less active or inactive.

Preferably, the compounds of the present invention prevent the protein-protein interaction between a sortilin molecule and a pro-neurotrophin or a p75NTR molecule, further preventing the formation of the apoptotic trimeric complex usually formed between sortilin, pro-neurotrophin and the p75NTR receptor, or resulting in the formation of a low affinity trimeric complex, which is biologically less active or inactive or has minimal activity.

Thus, the compound may bind to sortilin, a pro-neutrophin or a p75NTR molecule. The antagonistic action may be due to direct blocking of protein-protein interaction or it could be by steric hindrance when bound at a site of one of these proteins apart from the binding site.

According to a second aspect of the invention, there is provided a pharmaceutical composition comprising a compound according to the first aspect of the invention and one or more pharmaceutically acceptable carriers, excipients, and/or diluents.

In a third aspect of the invention, there is provided a compound according to the first aspect of the invention, or a pharmaceutical composition according to the second aspect of the invention for use in therapy.

According to a fourth aspect of the invention, there is provided a compound according to the first aspect of the invention, or a pharmaceutical composition according to the second aspect of the invention for use in the treatment or prevention of a neurodegenerative disorder, a cancer, pain, diabetes mellitus, diabetic retinopathy, cardiovascular disease, hereditary eye conditions or hearing loss.

Preferably, the neurodegenerative disorder is selected from frontotemporal dementia, Alzheimer's disease, Parkinson's disease and spinal cord injury.

Preferably, the hearing loss is selected from noise-induced hearing loss, ototoxicity induced hearing loss, age-induced hearing loss, idiopathic hearing loss, tinnitus and sudden hearing loss.

Preferably, the cancer is selected from breast cancer, lung cancer, ovarian cancer, prostate cancer, thyroid cancer, pancreatic cancer, glioblastoma, and colorectal cancer.

Preferably the cardiovascular disease is selected from atherosclerosis, cardiomyopathy, heard attack, arrhythmias, and coronary artery disease.

According to a fifth aspect of the invention, there is provided the use of the compound according to the first aspect of the invention for the manufacture of a medicament for the treatment or prevention of a neurodegenerative disorder, a cancer, pain, diabetes mellitus, diabetic retinopathy, cardiovascular disease, hereditary eye conditions or hearing loss.

According to a sixth aspect of the invention, there is provided a method for the treatment or prevention of a disease or condition responsive to sortilin modulation comprising administering a therapeutically effective amount of the compound according to the first aspect of the invention or the pharmaceutical composition according the second aspect of the invention.

The compounds of the invention may include isotopically-labelled and/or isotopically-enriched forms of the compounds. The compounds of the invention herein may contain unnatural proportions of atomic isotopes at one or more of the atoms that constitute such compounds. Examples of isotopes that can be incorporated into the disclosed compounds include isotopes of hydrogen, carbon, nitrogen, oxygen, phosphorus, sulfur, chlorine, such as $^{2}H$, $^{3}H$, $^{11}C$, $^{13}C$, $^{14}C$, $^{13}N$, $^{15}O$, $^{17}O$, $^{32}P$, $^{35}S$, $^{18}F$ , $^{36}Cl$.

The compounds of the invention may be used as such or, where appropriate, as pharmacologically acceptable salts (acid or base addition salts) thereof. The pharmacologically acceptable addition salts mentioned below are meant to comprise the therapeutically active non-toxic acid and base addition salt forms that the compounds are able to form. Compounds that have basic properties can be converted to their pharmaceutically acceptable acid addition salts by treating the base form with an appropriate acid. Exemplary acids include inorganic acids, such as hydrogen chloride, hydrogen bromide, hydrogen iodide, sulphuric acid, phosphoric acid; and organic acids such as formic acid, acetic acid, propanoic acid, hydroxyacetic acid, lactic acid, pyruvic acid, glycolic acid, maleic acid, malonic acid, oxalic acid, benzenesulphonic acid, toluenesulphonic acid, methanesulphonic acid, trifluoroacetic acid, fumaric acid, succinic acid, malic acid, tartaric acid, citric acid, salicylic acid, p-aminosalicylic acid, pamoic acid, benzoic acid, ascorbic acid and the like. Compounds that have acidic properties can be converted to their pharmaceutically acceptable basic addition salts by treating the acid form with an appropriate base. Exemplary base addition salt forms are the sodium, potassium, calcium salts, and salts with pharmaceutically acceptable amines such as, for example, ammonia, alkylamines, benzathine, and amino acids, such as, e.g. arginine and lysine. The term addition salt as used herein also comprises solvates which the compounds and salts thereof are able to form, such as, for example, hydrates, alcoholates and the like.

Throughout the present disclosure, a given chemical formula or name shall also encompass all pharmaceutically acceptable salts, solvates, hydrates, N-oxides, and/or prodrug forms thereof. It is to be understood that the compounds of the invention include any and all hydrates and/or solvates of the compound formulas. It is appreciated that certain functional groups, such as the hydroxy, amino, and like groups form complexes and/or coordination compounds with water and/or various solvents, in the various physical forms of the compounds. Accordingly, the above formulas are to be understood to include and represent those various hydrates and/or solvates.

Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, amide-imidic acid pairs, enamine-imine pairs, and annular forms where a proton can occupy two or more positions of a heterocyclic system, for example, 1H- and 3H-imidazole, 1H, 2H- and 4H- 1,2,4-triazole, 1H- and 2H- isoindole, and 1H- and 2H-pyrazole. Tautomeric forms can be in equilibrium or sterically locked into one form by appropriate substitution.

The compounds described herein can be asymmetric (e.g. having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically active starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis- and trans-geometric isomers of the compounds of the present invention are described and may be isolated as a mixture of isomers or as separated isomeric forms.

In the case of the compounds which contain an asymmetric carbon atom, the invention relates to the D form, the L form, and D,L mixtures and also, where more than one asymmetric carbon atom is present, to the diastereomeric forms. Those compounds of the invention which contain asymmetric carbon atoms, and which as a rule accrue as racemates, can be separated into the optically active isomers in a known manner, for example using an optically active acid. However, it is also possible to use an optically active starting substance from the outset, with a corresponding optically active or diastereomeric compound then being obtained as the end product.

The term "prodrugs" refers to compounds that may be converted under physiological conditions or by solvolysis to a biologically active compound of the invention. A prodrug may be inactive when administered to a subject in need thereof, but is converted in vivo to an active compound of the invention. Prodrugs are typically rapidly transformed in vivo to yield the parent compound of the invention, e.g. by hydrolysis in the blood. The prodrug compound usually offers advantages of solubility, tissue compatibility or delayed release in a mammalian organism (see Silverman, R. B., The Organic Chemistry of Drug Design and Drug Action, 2nd Ed., Elsevier Academic Press (2004), page 498 to 549). Prodrugs of a compound of the invention may be prepared by modifying functional groups, such as a hydroxy, amino or mercapto groups, present in a compound of the invention in such a way that the modifications are cleaved, either in routine manipulation or in vivo, to the parent compound of the invention. Examples of prodrugs include, but are not limited to, acetate, formate and succinate derivatives of hydroxy functional groups or phenyl carbamate derivatives of amino functional groups.

The term "treatment" as used herein may include prophylaxis of the named disorder or condition, or amelioration or elimination of the disorder once it has been established. The term "prevention" refers to prophylaxis of the named disorder or condition.

Methods delineated herein include those wherein the subject is identified as in need of a particular stated treatment. Identifying a subject in need of such treatment can be in the judgment of a subject or a health care professional and can be subjective (e.g. opinion) or objective (e.g. measurable by a test or diagnostic method).

In other aspects, the methods herein include those further comprising monitoring subject response to the treatment administrations. Such monitoring may include periodic imaging or sampling of subject tissue, fluids, specimens, cells, proteins, chemical markers, genetic materials, etc. as markers or indicators of the treatment regimen. In other methods, the subject is pre-screened or identified as in need of such treatment by assessment for a relevant marker or indicator of suitability for such treatment.

The invention provides a method of monitoring treatment progress. The method includes the step of determining a level of diagnostic marker (Marker) (e.g. any target or cell type delineated herein modulated by a compound herein) or diagnostic measurement (e.g., screen, assay) in a subject suffering from or susceptible to a disorder or symptoms thereof delineated herein, in which the subject has been administered a therapeutic amount of a compound herein sufficient to treat the disease or symptoms thereof. The level of Marker determined in the method can be compared to known levels of Marker in either healthy normal controls or in other afflicted patients to establish the subject's disease status. In preferred embodiments, a second level of Marker in the subject is determined at a time point later than the determination of the first level, and the two levels are compared to monitor the course of disease or the efficacy of the therapy. In certain preferred embodiments, a pre-treatment level of Marker in the subject is determined prior to beginning treatment according to this invention; this pre-treatment level of Marker can then be compared to the level of Marker in the subject after the treatment commences, to determine the efficacy of the treatment.

A level of Marker or Marker activity in a subject may be determined at least once. Comparison of Marker levels, e.g., to another measurement of Marker level obtained previously or subsequently from the same patient, another patient, or a normal subject, may be useful in determining whether therapy according to the invention is having the desired effect, and thereby permitting adjustment of dosage levels as appropriate. Determination of Marker levels may be performed using any suitable sampling/expression assay method known in the art or described herein. Preferably, a tissue or fluid sample is first removed from a subject. Examples of suitable samples include blood, urine, tissue, mouth or cheek cells, and hair samples containing roots. Other suitable samples would be known to the person skilled in the art. Determination of protein levels and/or mRNA levels (e.g., Marker levels) in the sample can be performed using any suitable technique known in the art, including, but not limited to, enzyme immunoassay, is ELISA, radiolabeling/assay techniques, blotting/chemiluminescence methods, real-time PCR, and the like.

For clinical use, the compounds disclosed herein are formulated into pharmaceutical compositions (or formulations) for various modes of administration. It will be appreciated that compounds of the invention may be administered together with a physiologically acceptable carrier, excipient, and/or diluent (i.e. one, two, or all three of these). The pharmaceutical compositions disclosed herein may be administered by any suitable route, preferably by oral, rectal, nasal, topical (including ophthalmic, buccal and sublingual), sublingual, transdermal, intrathecal, transmucosal or parenteral (including subcutaneous, intramuscular, intravenous and intradermal) administration. Other formulations may conveniently be presented in unit dosage form, e.g., tablets and sustained release capsules, and in liposomes, and may be prepared by any methods well known in the art of pharmacy. Pharmaceutical formulations are usually prepared by mixing the active substance, or a pharmaceutically acceptable salt thereof, with conventional pharmaceutically acceptable carriers, diluents or excipients. Examples of excipients are water, gelatin, gum arabicum, lactose, microcrystalline cellulose, starch, sodium starch glycolate, calcium hydrogen phosphate, magnesium stearate, talcum, colloidal silicon dioxide, and the like. Such formulations may also contain other pharmacologically active agents, and conventional additives, such as stabilizers, wetting agents, emulsifiers, flavouring agents, buffers, and the like. Usually, the amount of active compounds is between 0.1-95% by weight of the preparation, preferably between 0.2-20% by weight in preparations for parenteral use and more preferably between 1-50% by weight in preparations for oral administration. The formulations can be further prepared by known methods such as granulation, compression, microencapsulation, spray coating, etc. The formulations may be prepared by conventional methods in the dosage form of tablets, capsules, granules, powders, syrups, suspensions, suppositories or injections. Liquid formulations may be prepared by dissolving or suspending the active substance in water or other suitable vehicles. Tablets and granules may be coated in a conventional manner. To maintain therapeutically effective plasma concentrations for extended periods of time, compounds disclosed herein may be incorporated into slow release formulations.

The dose level and frequency of dosage of the specific compound will vary depending on a variety of factors including the potency of the specific compound employed, the metabolic stability and length of action of that compound, the patient's age, body weight, general health, sex, diet, mode and time of administration, rate of excretion, drug combination, the severity of the condition to be treated, and the patient undergoing therapy. The daily dosage may, for example, range from about 0.001 mg to about 100 mg per kilo of body weight, administered singly or multiply in doses, e.g. from about 0.01 mg to about 25 mg each. Normally, such a dosage is given orally but parenteral administration may also be chosen.

DEFINITIONS

"Optional" or "optionally" means that the subsequently described event or circumstance may, but need not, occur, and that the description includes instances where the event or circumstance occurs and instances in which it does not.

The term "heteroatom" means O, N, or S.

The term "$C_1$-$C_4$ alkyl" denotes a straight, branched or cyclic or partially cyclic alkyl group having from 1 to 4 carbon atoms, i.e. 1, 2, 3 or 4 carbon atoms. For the "$C_1$-$C_4$ alkyl" group to comprise a cyclic portion it should be formed of 3 to 4 carbon atoms. For parts of the range "$C_1$-$C_4$ alkyl" all subgroups thereof are contemplated, such as $C_1$-$C_4$ alkyl, $C_1$-$C_3$ alkyl, $C_1$-$C_2$ alkyl, $C_1$ alkyl, $C_2$-$C_4$ alkyl, $C_2$-$C_3$ alkyl, $C_2$ alkyl, $C_3$-$C_4$ alkyl, $C_3$ alkyl and $C_4$ alkyl. Examples of "$C_1$-$C_4$ alkyl" include methyl, ethyl, n-propyl, isopropyl, cyclopropyl, n-butyl, isobutyl, sec-butyl, t-butyl, cyclobutyl and cyclopropylmethyl.

The term "$C_1$-$C_4$ hydroxyalkyl" denotes a $C_1$-$C_4$ alkyl as described above substituted with an —OH group. Examples of "$C_1$-$C_4$ hydroxyalkyl" include hydroxymethyl, 1-hydroxyethyl, 2-hydroxyethyl, 1-hydroxypropyl, 2-hydroxypropyl and 3-hydroxypropyl.

The term "$C_1$-$C_4$ aminoalkyl" denotes a $C_1$-$C_4$ alkyl as described above substituted with an —$NH_2$ group.

The term "$C_1$-$C_4$ haloalkyl" denotes a $C_1$-$C_4$ alkyl as described above substituted with a halogen atom, which is preferably, F, Cl, Br and I, more preferably F and Cl, and most preferably F.

The term "$C_1$-$C_4$ alkyl" denotes a straight, branched or cyclic or partially cyclic alkyl group having from 1 to 6 carbon atoms, i.e. 1, 2, 3, 4, 5 or 6 carbon atoms. For the "$C_1$-$C_6$ alkyl" group to comprise a cyclic portion it should be formed of 3 to 6 carbon atoms. For parts of the range "$C_1$-$C_6$ alkyl" all subgroups thereof are contemplated, such as $C_1$-$C_5$ alkyl, $C_1$-$C_4$ alkyl, $C_1$-$C_3$ alkyl, $C_1$-$C_2$ alkyl, $C_1$ alkyl, $C_2$-$C_6$ alkyl, $C_2$-$C_5$ alkyl, $C_2$-$C_4$ alkyl, $C_2$-$C_3$ alkyl, $C_2$ alkyl, $C_3$-$C_6$ alkyl, $C_3$-$C_5$ alkyl, $C_3$-$C_4$ alkyl, $C_3$ alkyl, $C_4$-$C_6$ alkyl, $C_4$-$C_5$ alkyl, $C_4$ alkyl, $C_5$ -$C_6$ alkyl, $C_5$ alkyl, and $C_6$ alkyl. Examples of "$C_1$-$C_6$ alkyl" include methyl, ethyl, n-propyl, isopropyl, cyclopropyl, n-butyl, isobutyl, sec-butyl, t-butyl, cyclobutyl, cyclopropylmethyl, and straight, branched or cyclic or partially cyclic pentyl and hexyl etc.

When a term denotes a range, for instance "1 to 6 carbon atoms" in the definition of $C_1$-$C_6$ alkyl, each integer is considered to be disclosed, i.e. 1, 2, 3, 4, 5 and 6.

The term "$C_2$-$C_6$ alkenyl" denotes a straight, branched or cyclic or partially cyclic alkyl group having at least one carbon-carbon double bond, and having from 2 to 6 carbon atoms. The alkenyl group may comprise a ring formed of 3 to 6 carbon atoms. For parts of the range "$C_2$-$C_6$ alkenyl" all subgroups thereof are contemplated, such as $C_2$-$C_5$ alkenyl, $C_2$-$C_5$ alkenyl, $C_2$-$C_3$ alkenyl, $C_2$ alkenyl, $C_3$-$C_6$ alkenyl, $C_3$-$C_5$ alkenyl, $C_3$-$C_4$ alkenyl, $C_3$ alkenyl, $C_4$-$C_6$ alkenyl, $C_4$-$C_5$ alkenyl, $C_4$ alkenyl, $C_5$-$C_6$ alkenyl, $C_5$ alkenyl, and $C_6$ alkenyl. Examples of "$C_2$-$C_6$ alkenyl" include 2-propenyl, 2-butenyl, 3-butenyl, 2-methyl-2-propenyl, 2-hexenyl, 5-hexenyl, 2,3-dimethyl-2-butenyl.

The term "$C_1$-$C_4$ alkoxy" denotes —O—($C_1$-$C_4$alkyl) in which a $C_1$-$C_4$ alkyl group is as defined above and is attached to the remainder of the compound through an oxygen atom. Examples of "$C_1$-$C_4$ alkoxy" include methoxy, ethoxy, n-propoxy, isopropoxy, n-butoxy, isobutoxy, sec-butoxy and t-butoxy.

The term "$C_1$-$C_4$ haloalkoxy" denotes a $C_1$-$C_4$ alkoxy as described above substituted with a halogen atom, which is preferably, F, Cl, Br and I, more preferably F and Cl, and most preferably F.

The term "halo" means a halogen atom, and is preferably, F, Cl, Br and I, more preferably F and Cl, and most preferably F.

The term "5- to 7-membered monocyclic heterocyclic ring" denotes a non-aromatic monocyclic ring system having 5 to 7 ring atoms, in which at least one ring atoms is a heteroatom.

"An effective amount" refers to an amount of a compound of the invention that confers a therapeutic effect on the treated subject. The therapeutic effect may be objective (i.e. measurable by some test or marker) or subjective (i.e. subject gives an indication of or feels an effect).

As used herein, the terms "administration" or "administering" mean a route of administration for a compound disclosed herein. Exemplary routes of administration include, but are not limited to, oral, intraocular, intravenous, intraperitoneal, intraarterial, and intramuscular. The preferred route of administration can vary depending on various factors, e.g. the components of the pharmaceutical composition comprising a compound disclosed herein, site of the potential or actual disease and severity of disease.

The terms "subject" and "patient" are used herein interchangeably. They refer to a human or another mammal (e.g., mouse, rat, rabbit, dog, cat, cattle, swine, sheep, horse or primate) that can be afflicted with or is susceptible to a disease or disorder but may or may not have the disease or disorder. It is preferred that the subject is human.

Compounds of the invention may be disclosed by the name or chemical structure. If a discrepancy exists between the name of a compound and its associated chemical structure, then the chemical structure prevails.

The invention will now be further illustrated by the following non-limiting examples. The specific examples below are to be construed as merely illustrative, and not limitative of the remainder of the disclosure in any way whatsoever. Without further elaboration, it is believed that one skilled in the art can, based on the description herein, utilise the present invention to its fullest extent. All references and publications cited herein are hereby incorporated by reference in their entirety.

PREPARATION OF COMPOUNDS OF THE INVENTION

The compounds of formula (I) disclosed herein may be prepared by, or in analogy with, conventional methods. Appropriate reaction conditions for the individual reaction steps are known to a person skilled in the art. The necessary starting materials for preparing the compounds of formula (I) are either commercially available, or may be prepared by methods known in the art.

The compounds of formula (I) may possess one or more chiral carbon atoms, and they may therefore be obtained in the form of optical isomers, e.g., as a pure enantiomer, or as a mixture of enantiomers or as a mixture containing diastereomers. The separation of mixtures of optical isomers to obtain pure enantiomers is well known in the art and may, for example, be achieved by fractional crystallization of salts with optically active (chiral) acids or by chromatographic separation on chiral columns.

Particular experimental procedures for examples of the invention are described below. The processes may be carried out to give a compound of the invention in the form of a neutral molecule, for example as a protonated carboxylic acid or free base, or as an ionic molecule with a basic or acid addition salt respectively. A pharmaceutically acceptable basic or acid addition salt may be obtained by dissolving the free base in a suitable organic solvent and treating the solution with a base or an acid, in accordance with conventional procedures for preparing basic and acid addition salts from acid or base compounds. Examples of addition salt forming acids are mentioned above.

The chemicals used in the synthetic routes delineated herein may include, for example, solvents, reagents, catalysts, and protecting group and deprotecting group reagents. Examples of protecting groups are t-butoxycarbonyl (Boc), benzyl and trityl(triphenylmethyl). The methods described below may also additionally include steps, either before or after the steps described specifically herein, to add or remove suitable protecting groups in order to ultimately allow synthesis of the compounds. In addition, various synthetic steps may be performed in an alternate sequence or order to give the desired compounds. Synthetic chemistry transformations and protecting group methodologies (protection and deprotection) useful in synthesizing applicable compounds are known in the art and include, for example, those described in R. Larock, *Comprehensive Organic Transformations*, VCH Publishers (1989); T. W. Greene and P. G. M. Wuts, *Protective Groups in Organic Synthesis,* 3rd Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

The invention will now be further illustrated by the following non-limiting examples. The specific examples below are to be construed as merely illustrative, and not !imitative of the remainder of the disclosure in any way whatsoever. Without further elaboration, it is believed that one skilled in the art can, based on the description herein, utilize the present invention to its fullest extent. All references and publications cited herein are hereby incorporated by reference in their entirety.

Scheme 1

GENERAL SYNTHETIC PROCEDURE 1

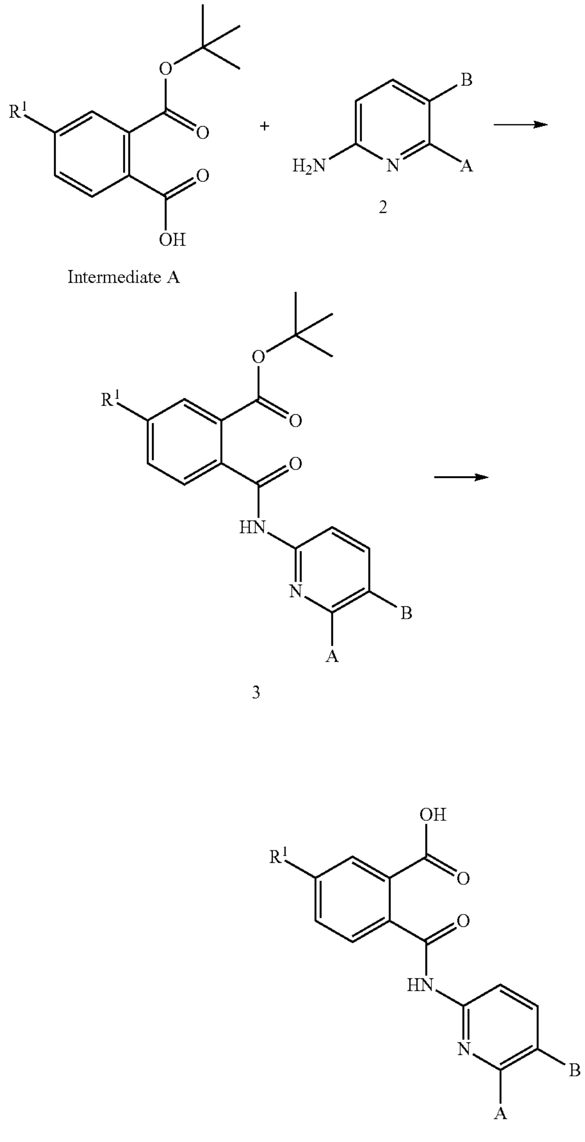

Intermediate A

2

3

I

In general synthetic procedure 1, the free carboxylic acid present in Intermediate A is coupled with a suitably substituted amino pyridine using standard amide coupling techniques, for example by mixing a compound like Intermediate A and a suitable 2-aminopyridine 2 in the presence a coupling agent such as HATU and a nitrogen containing amine, such as DIPEA in a suitable organic solvent, such as DMF, at room temperature to afford an intermediate of general formula 3. The compounds of general formula I can, then, be obtained from 3, by deprotection of the tent-butyl ester group using, for example, neat formic acid.

Intermediate A, can be obtained, as shown in Scheme 2, with the required, regiochemical substitution pattern, from commercially available compounds of general structure 4, 5 or 6. When starting from intermediates of general structure 4, the carboxylic acid can be activated with a chlorinating reagent, for example thionyl chloride, in a suitable solvent such as dichloromethane. This provides intermediates of general structure 5 that upon treatment with a metal salt of tent-butanol, such as sodium or potassium tert-butanoate in a suitable solvent such as tent-butanol, to afford intermediate 6. Benzylic oxidation of the methyl substituent to the carboxylic acid general structure as shown in Intermediate A, can be achieved, for example, by chemoselective bromination to give general intermediate 7, using a brominating reagent like for example N-bromosuccinimide. The benzyl bromide, in 7, can yield the aldehyde containing intermediate of general structure 8, by reaction with an oxidizing reagent, for example N-methylmorpholine N-oxide, (NMO). Intermediate A can be then obtained by a secondary oxidation of the aldehyde functionality present in intermediate of general formula 8 with the appropriate oxidizing system, for illustration by using a mixture of sodium chlorite, sodium dihydrogen phosphate and 2-methyl-2-butene in a suitable solvent like, for example, a mixture of t-butanol and water.

Scheme 2

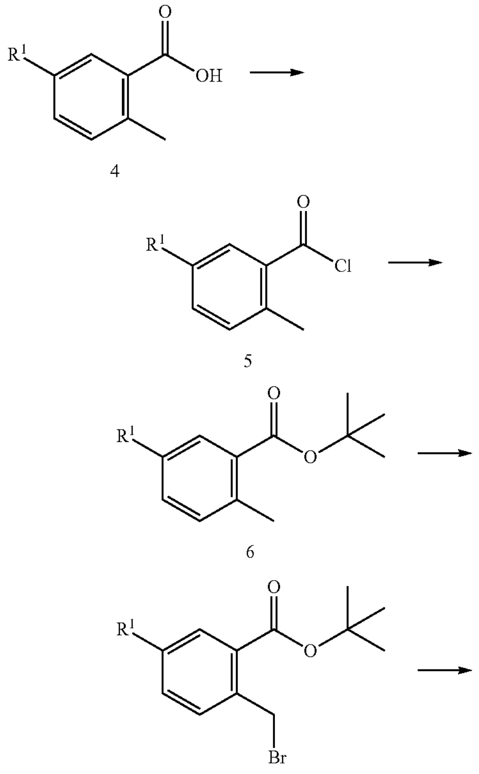

4

5

6

7

-continued

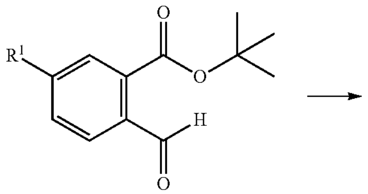

8

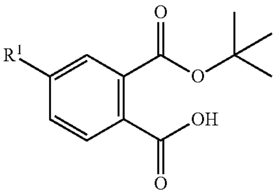

Intermediate A

Scheme 3

GENERAL SYNTHETIC PROCEDURE 2

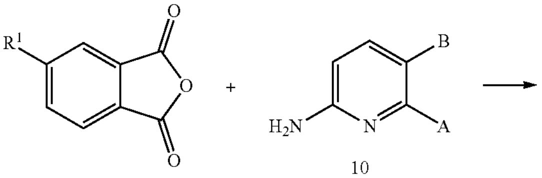

9 10

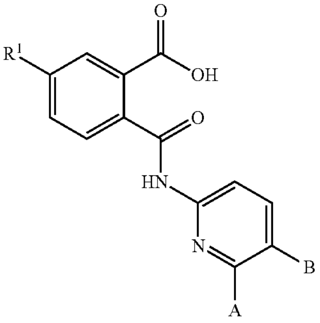

I

In general synthetic procedure 2, a phthalic anhydride of general structure 9 is reacted with a suitably substituted 2-aminopyridine followed by separation of the two regioisomeric amides by chromatography, for example by using supercritical fluid chromatography (SFC), to produce the desired compound of general structure I.

EXAMPLES

Scheme 4

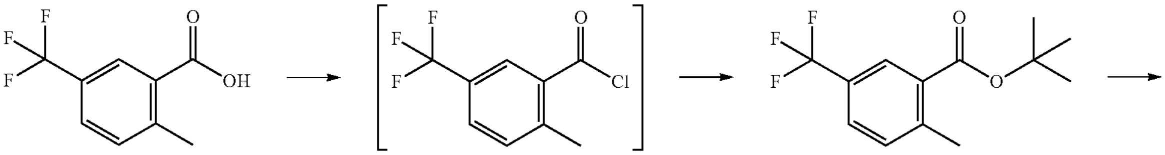

11 12 13

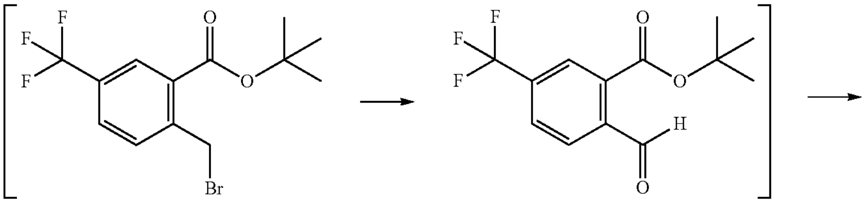

14 15

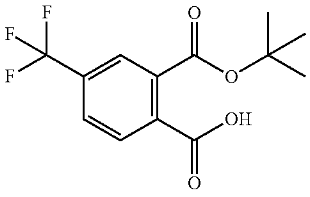 [SMILES: CC(C)(C)OC(=O)c1cc(C(F)(F)F)ccc1C(=O)O]

Intermediate A1

Intermediate 1A 2-(tert-butoxycarbonyl)-4-(trifluoromethyl) benzoic acid

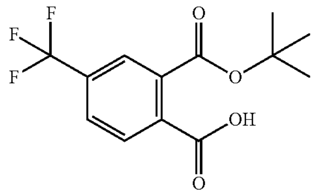

Synthesised According to Scheme 4.

Oxalyl dichloride (3.73 g, 2.52 mL, 1.2 Eq, 29.4 mmol) was added to a stirred suspension of 2-methyl-5-(trifluoromethyl)benzoic acid (5.00 g, 1 Eq, 24.5 mmol) and N,N-dimethylformamide (35.8 mg, 37.9 μL, 0.02 Eq, 490 pmol) in anhydrous dichloromethane (100 ml) at room temperature under nitrogen. Vigorous effervescence was observed and after 10 minutes all solid had dissolved. After 2 hours effervescence had stopped and tent-butanol (9.08 g, 11.7 mL, 5 Eq, 122 mmol) followed by pyridine (2.32 g, 2.38 mL, 1.2 Eq, 29.4 mmol) were added. The resulting solution was stirred at room temperature for 18 hours then heated to 35° C. for 4 days. Most of the dichloromethane was evaporated in vacuo. The mixture was diluted with TBME (100 ml), washed with 1M hydrochloric acid (50 ml) then sodium bicarbonate solution (50 ml) then brine (25 ml), dried ($MgSO_4$) and evaporated in vacuo to a crude solid 13 (5.001 g), $^1$H NMR was consistent with a mixture of tent-butyl ester and dimer acid anhydride. The solid was dissolved in TBME (100 ml) and N,N-dimethylethylenediamine (1.00g) was added. After 30 minutes, complete conversion of the anhydride to the corresponding ester and carboxylic acid was achieved. The solution was washed with 1M hydrochloric acid (50 ml), sodium bicarbonate solution (50 ml), brine (25 ml), dried ($MgSO_4$) and evaporated in vacuo to an oil to yield intermediate 13 (3.31g)

$^1$H NMR in DMSO-d: (400 MHz, DMSO-d6) δ7.96 (d, J=2.1 Hz, 1H), 7.80 (dd, J=8.1, 2.1 Hz, 1H), 7.55 (d, J=8.0 Hz, 1H), 2.56 (s, 3H), 1.55 (s, 9H).

N-bromosuccinimide (2.46 g, 1.20 Eq, 13.8 mmol) was added to a stirred solution of tert-butyl 2-methyl-5-(trifluoromethyl)benzoate 13 (3.16 g, 95% Wt, 1.00 Eq, 11.5 mmol) in Chloroform (60 mL). The mixture was heated to reflux and AIBN (94.7 mg, 0.05 Eq, 577 μmol) was added. After 30 minutes there was evidence of reaction by thin layer chromatography (silica plate,9/1 hexane/ethyl acetate) indicating formation of a close-running product. The mixture was cooled to room temperature and the chloroform removed in vacuo. The residue was redissolved in anhydrous Acetonitrile (60 mL) and 4-methylmorpholine 4-oxide (2.70 g, 2.00 Eq, 23.1 mmol) added. The mixture was stirred at room temperature for 20 hours. The mixture was diluted with TBME (120 ml), washed with 1M hydrochloric acid (60 ml) then 1M sodium hydroxide solution (60 ml) then brine (60 ml), dried ($MgSO_4$) and evaporated in vacuo to intermediate 15 as an oil (2.83g) $^1$H NMR in DMSO-d6 was consistent with product structure at estimated purity ca. 25% purity. This material was taken directly to next stage without further purification.

Sodium chlorite (467 mg, 2.00 Eq, 5.16 mmol) was added to a stirred solution of crude tert-butyl 2-formyl-5-(trifluoromethyl) benzoate (2.83 g, 25% Wt, 1.00 Eq, 2.58 mmol), sodium dihydrogen phosphate (310 mg, 1.00 Eq, 2.58 mmol) and 2-methyl-2-butene (905 mg, 1.37 mL, 5.00 Eq, 12.9 mmol) in a mixture of t-butanol (4 mL) and water (1 mL). The reaction mixture was stirred for 18 hours at room temperature then extra sodium chlorite (467 mg, 2.00 Eq, 5.16 mmol) was added and stirring continued for 2 hours whereupon reaction was complete. The mixture was diluted with ethyl acetate (50 ml), washed with a mixture of 1M hydrochloric acid (40 ml) and sodium metabisulphite solution (10 ml), dried ($MgSO_4$) and evaporated in vacuo. The residue was subjected to column chromatography (40 g Flash Pure silica cartridge) with liquid loading in dichloromethane/isohexane (1:2, 6 ml) followed by elution with a 0-50% gradient of 99/1 ethyl acetate/acetic acid in isohexane. Fractions containing the desired product were evaporated in vacuo and the residue co-evaporated with toluene (10 ml) to give Intermediate A1 an oil that solidified (0.638 g, 2.1mmol, 81%, 95% Purity).

Preparation of Example 1

2-((5,8-dihydro-6H-pyrano[3,4-b]pyridin-2-yl)carbamoyl)-5-(trifluoromethyl)benzoic acid

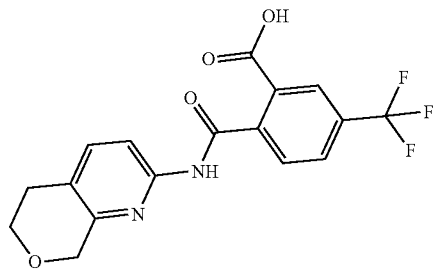 [SMILES: O=C(O)c1cc(C(F)(F)F)ccc1C(=O)Nc1ccc2c(n1)COCC2]

Intermediate 17

Tert-butyl 2-({5H,6H,8H-pyrano[3,4-b]pyridin-2-yl}carbamoyl)-5-(trifluoromethyl)benzoate

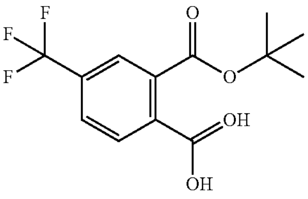

Intermediate A1

+

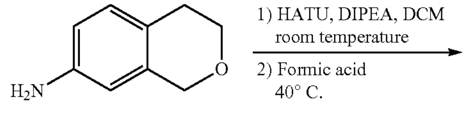

16

-continued

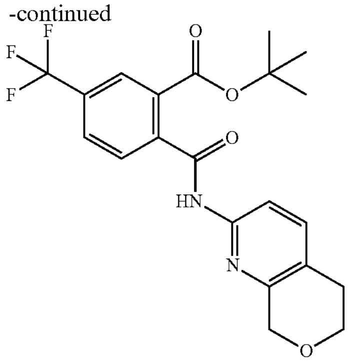

17

HATU (72.1 mg, 0.19 mmol, 1.1 equiv.) was added to a mixture of 2-(tert-butoxycarbonyl)-4-(trifluoromethyl)benzoic acid (50 mg, 0.17 mmol), 5,8-dihydro-6H-pyrano[3,4-b]pyridin-2-amine (28.5 mg, 0.19 mmol, 1 equiv.) and diisopropylethylamine (90 μl, 0.52 mmol, 3 equiv.) in dichloromethane (1 mL) was added and the mixture was stirred for 16 hours at room temperature.

Formic acid (2 mL) was added and the mixture was stirred at 40° C. for 24 hours. The solvent was evaporated in vacuo and residue was taken up in DMSO (1 mL) and purified by preparative HPLC, (Method PREP_ACID-AS4A). The product containing fractions were combined and lyophilised resulting in 14 mg (0.04 mmol, 11% of theory) of the title compound.

LCMS (Method 3: UPLC_AN_BASE, 0.836 min; M+H=367.2; calculated. 367.1) $^1$H NMR (400 MHz, DMSO) δ13.54 (s, 1H), 10.99 (s, 1H), 8.12 (d, J=1.9 Hz, 1H), 8.01 (d, J=7.8 Hz, 2H), 7.74 (d, J=8.0 Hz, 1H), 7.63 (d, J=8.4 Hz, 1H), 4.58 (s, 2H), 3.90 (t, J=5.6 Hz, 2H), 2.83-2.76 (m, 2H).

Examples 2 to 23

Examples 2 to 23 depicted in Table 1, can be prepared in accordance with general synthetic procedures 1 and/or 2.

TABLE 1

| Ex. | Compound Name | Structure |
|---|---|---|
| 2 | 2-({5H,6H,8H-pyrano[3,4-b]pyridin-2-yl}carbamoyl)-5-(trifluoromethyl)benzoic acid | 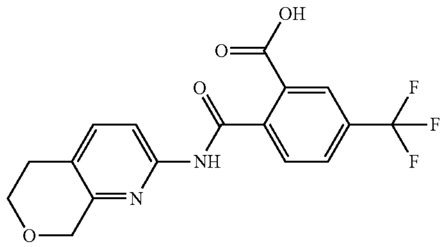 [SMILES: O=C(O)c1cc(C(F)(F)F)ccc1C(=O)Nc1ccc2c(n1)COCC2] |
| 3 | 2-{[6-(hydroxymethyl)pyridin-2-yl]carbamoyl}-5-(trifluoromethyl)benzoic acid | 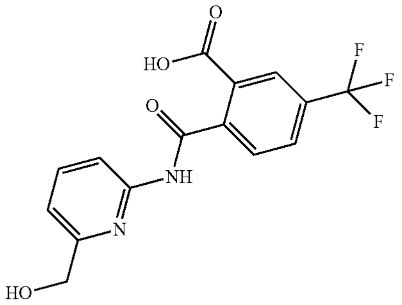 [SMILES: O=C(O)c1cc(C(F)(F)F)ccc1C(=O)Nc1cccc(CO)n1] |
| 4 | 5-tert-butyl-2-{[6-(hydroxymethyl)pyridin-2-yl]carbamoyl}benzoic acid | 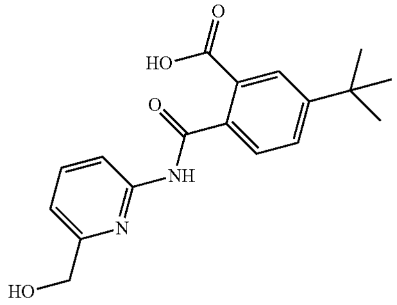 [SMILES: CC(C)(C)c1ccc(C(=O)Nc2cccc(CO)n2)c(C(=O)O)c1] |

TABLE 1-continued
| Ex. | Compound Name | Structure |
| --- | --- | --- |
| 5 | (RAC) 2-{[6-(1-hydroxyethyl)pyridin-2-yl]carbamoyl}-5-(trifluoromethyl)benzoic acid | 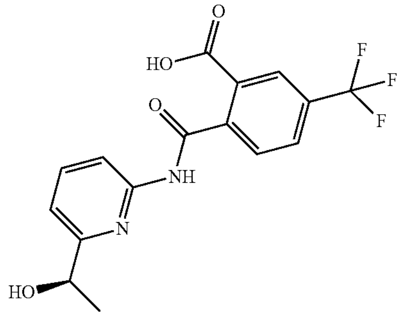 [SMILES: C[C@@H](O)c1cccc(NC(=O)c2ccc(C(F)(F)F)cc2C(=O)O)n1] |
| 6 | 2-({6-[(1S)-1-hydroxyethyl]pyridin-2-yl}carbamoyl)-5-(trifluoromethyl)benzoic acid | 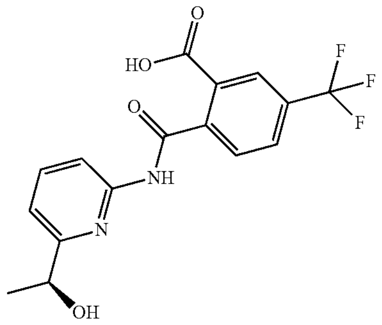 [SMILES: C[C@H](O)c1cccc(NC(=O)c2ccc(C(F)(F)F)cc2C(=O)O)n1] |
| 7 | 2-({6-[(1R)-1-hydroxyethyl]pyridin-2-yl}carbamoyl)-5-(trifluoromethyl)benzoic acid | 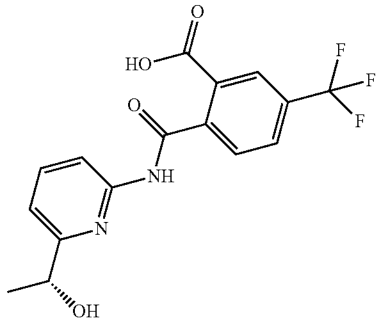 [SMILES: C[C@@H](O)c1cccc(NC(=O)c2ccc(C(F)(F)F)cc2C(=O)O)n1] |
| 8 | 2-{[6-(2-hydroxypropan-2-yl)pyridin-2-yl]carbamoyl}-5-(trifluoromethyl)benzoic acid | 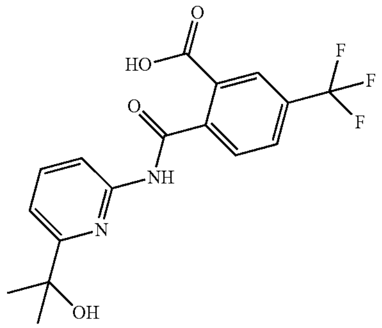 [SMILES: CC(C)(O)c1cccc(NC(=O)c2ccc(C(F)(F)F)cc2C(=O)O)n1] |

TABLE 1-continued

| Ex. | Compound Name | Structure |
|---|---|---|
| 9 | 2-{[6-(2-hydroxyethyl)pyridin-2-yl]carbamoyl}-5-(trifluoromethyl)benzoic acid | 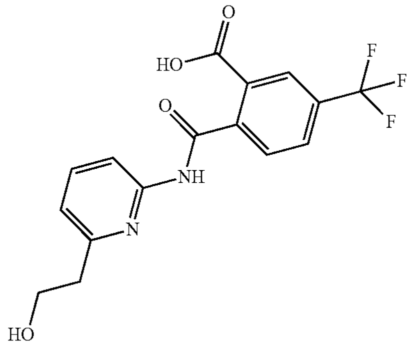 [SMILES: O=C(O)c1cc(C(F)(F)F)ccc1C(=O)Nc1cccc(CCO)n1] |
| 10 | (RAC) 5-tert-butyl-2-{[6-(1-hydroxyethyl)pyridin-2-yl]carbamoyl}benzoic acid | 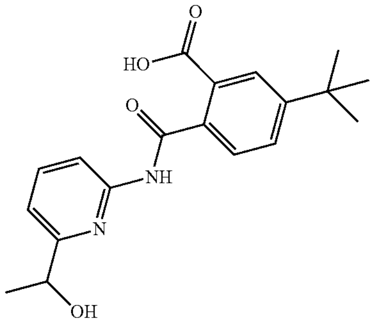 [SMILES: CC(O)c1cccc(NC(=O)c2ccc(C(C)(C)C)cc2C(=O)O)n1] |
| 11 | 5-tert-butyl-2-({6-[(1R)-1-hydroxyethyl]pyridin-2-yl}carbamoyl)benzoic acid | 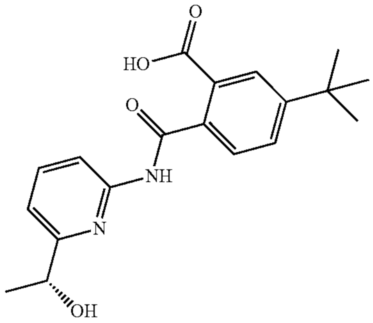 [SMILES: C[C@@H](O)c1cccc(NC(=O)c2ccc(C(C)(C)C)cc2C(=O)O)n1] |
| 12 | 5-tert-butyl-2-({6-[(1S)-1-hydroxyethyl]pyridin-2-yl}carbamoyl)benzoic acid | 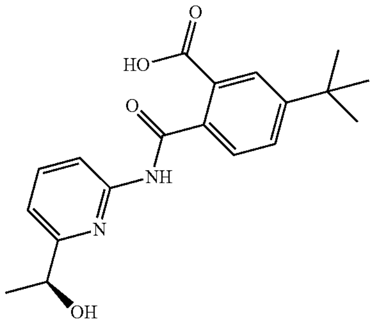 [SMILES: C[C@H](O)c1cccc(NC(=O)c2ccc(C(C)(C)C)cc2C(=O)O)n1] |
| 13 | 2-({2H,3H,4H-pyrano[2,3-b]pyridin-7-yl}carbamoyl)-5-(trifluoromethyl)benzoic acid | 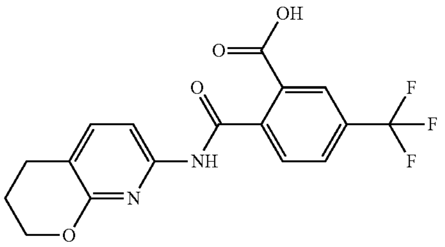 |

TABLE 1-continued

| Ex. | Compound Name | Structure |
|---|---|---|
| 14 | 2-({2H,3H-[1,4]dioxino[2,3-b]pyridin-6-yl}carbamoyl)-5-(trifluoromethyl)benzoic acid | 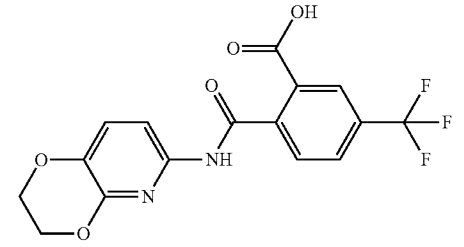 [SMILES: O=C(O)c1cc(C(F)(F)F)ccc1C(=O)Nc1ccc2c(n1)OCCC2] |
| 15 | 2-({5H,7H,8H-pyrano[4,3-b]pyridin-2-yl}carbamoyl)-5-(trifluoromethyl)benzoic acid | 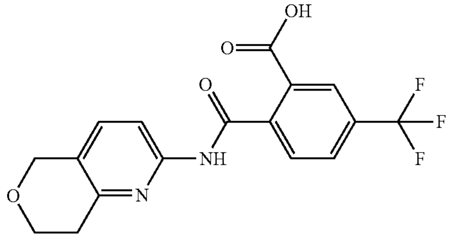 [SMILES: O=C(O)c1cc(C(F)(F)F)ccc1C(=O)Nc1ccc2c(n1)CCOC2] |
| 16 | 2-[(5,6,7,8-tetrahydro-1,6-naphthyridin-2-yl)carbamoyl]-5-(trifluoromethyl)benzoic acid | 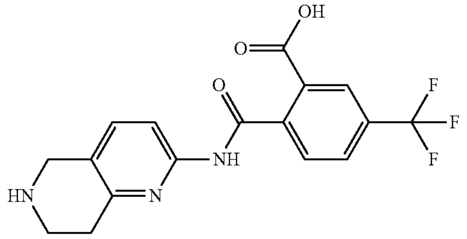 [SMILES: O=C(O)c1cc(C(F)(F)F)ccc1C(=O)Nc1ccc2c(n1)CCNC2] |
| 17 | 5-tert-butyl-2-({5H,6H,8H-pyrano[3,4-b]pyridin-2-yl}carbamoyl)benzoic acid | 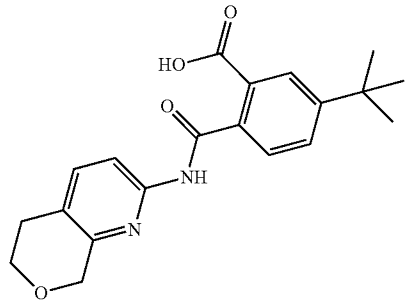 [SMILES: CC(C)(C)c1ccc(C(=O)Nc2ccc3c(n2)COCC3)c(C(=O)O)c1] |
| 18 | (RAC) 2-{[6-(2,2,2-trifluoro-1-hydroxyethyl)pyridin-2-yl]carbamoyl}-5-(trifluoromethyl)benzoic acid | 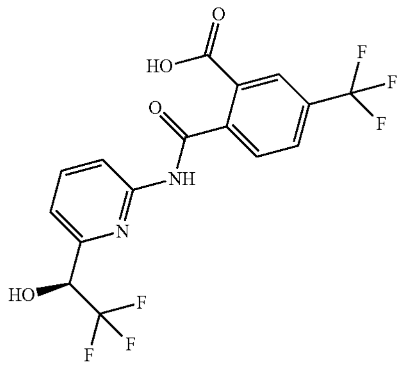 [SMILES: O=C(O)c1cc(C(F)(F)F)ccc1C(=O)Nc1cccc([C@H](O)C(F)(F)F)n1] |

TABLE 1-continued
| Ex. | Compound Name | Structure |
|---|---|---|
| 19 | 2-({6-[(1S)-2,2,2-trifluoro-1-hydroxyethyl]pyridin-2-yl}carbamoyl)-5-(trifluoromethyl)benzoic acid | 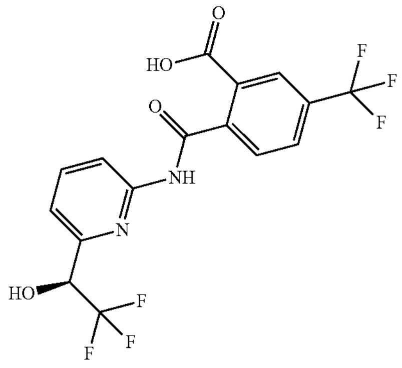 [SMILES: O=C(O)c1cc(C(F)(F)F)ccc1C(=O)Nc1cccc([C@H](O)C(F)(F)F)n1] |
| 20 | 2-({6-[(1R)-2,2,2-trifluoro-1-hydroxyethyl]pyridin-2-yl}carbamoyl)-5-(trifluoromethyl)benzoic acid | 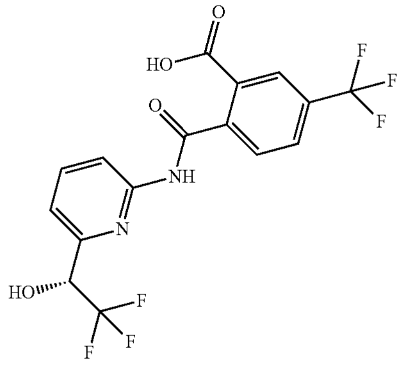 [SMILES: O=C(O)c1cc(C(F)(F)F)ccc1C(=O)Nc1cccc([C@@H](O)C(F)(F)F)n1] |
| 21 | (RAC) 2-{[6-(1-amino-2,2,2-trifluoroethyl)pyridin-2-yl]carbamoyl}-5-(trifluoromethyl)benzoic acid | 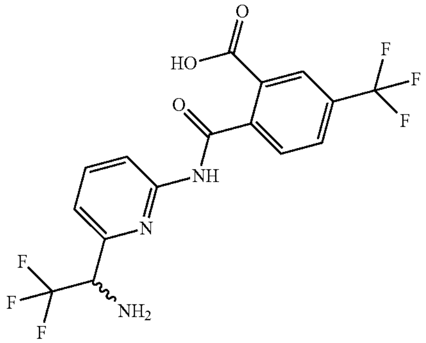 [SMILES: NC(c1cccc(NC(=O)c2ccc(C(F)(F)F)cc2C(=O)O)n1)C(F)(F)F] |
| 22 | 2-({6-[(1R)-1-amino-2,2,2-trifluoroethyl]pyridin-2-yl}carbamoyl)-5-(trifluoromethyl)benzoic acid | 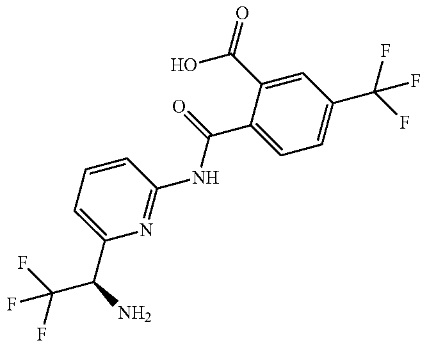 [SMILES: N[C@H](c1cccc(NC(=O)c2ccc(C(F)(F)F)cc2C(=O)O)n1)C(F)(F)F] |

TABLE 1-continued

| Ex. | Compound Name | Structure |
|---|---|---|
| 23 | 2-({6-[(1S)-1-amino-2,2,2-trifluoroethyl]pyridin-2-yl}carbamoyl)-5-(trifluoromethyl)benzoic acid | 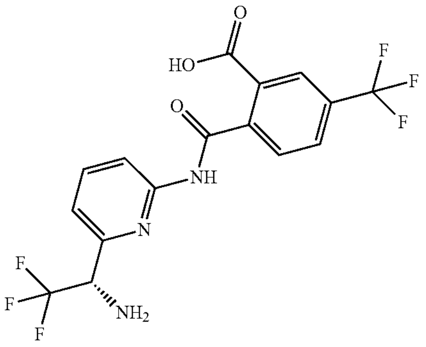 [SMILES: N[C@@H](c1cccc(NC(=O)c2ccc(C(F)(F)F)cc2C(=O)O)n1)C(F)(F)F] |
| 24 | 2-{[6-(methoxymethyl)pyridin-2-yl]carbamoyl}-5-(trifluoromethyl)benzoic acid | 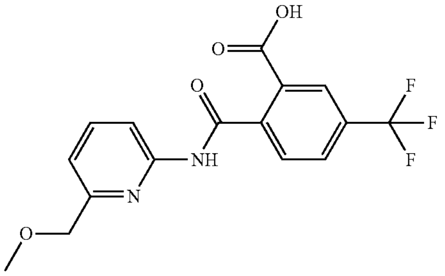 [SMILES: COCc1cccc(NC(=O)c2ccc(C(F)(F)F)cc2C(=O)O)n1] |
| 25 | 5-tert-butyl-2-{[6-(methoxymethyl)pyridin-2-yl]carbamoyl}benzoic acid | 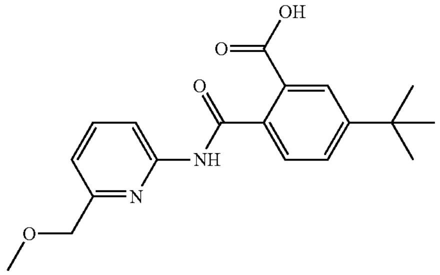 [SMILES: COCc1cccc(NC(=O)c2ccc(C(C)(C)C)cc2C(=O)O)n1] |

Analytical Methods

LC-MS

Method Information

Method 1: LCMS_SC_BASE, Apparatus: Agilent 1260 Bin. Pump: G1312B, degasser; autosampler, ColCom, DAD: Agilent G1315C, 210, 220 and 220-320 nm, PDA 210-320 nm, MSD: Agilent LC/MSD G6130B ESI, pos/neg 100-1000; column: Waters XSelect™ CSH C18, 30x2.1 mm, 3.5 μm, Temp: 25° C., Flow: 1 mL/min, Gradient: t0=5% B, t1.6 min=98% B, t3 min=98% B, Post-time: 1.4 min, Eluent A: 10 mM ammonium bicarbonate in water (pH=9.0), Eluent B: acetonitrile.

Method 2: UPLC_SC_BASE, Apparatus: Waters IClass; Bin. Pump: UPIBSM, SM: UPISMFTN with SO; UPCMA, PDA: UPPDATC, 210-320 nm, SQD: ACQ-SQD2 ESI; ELSD: gas pressure 40 psi, drift tube temp: 50° C., column: Waters XSelect CSH C18, 50'2.1 mm, 2.5 μm, Temp: 25° C., Flow: 0.6 mL/min, Gradient: t0=5% B, t1.3 min=98% B, t1.7 min=98% B, Post-time: 0.3 min, Eluent A: 10 mM ammonium bicarbonate in water (pH=9.5), Eluent B: acetonitrile.

Method 3: UPLC_AN_BASE, Apparatus: Waters IClass; Bin. Pump: UPIBSM, SM: UPISMFTN with SO; UPCMA, PDA: UPPDATC, 210-320 nm, SQD: ACQ-SQD2 ESI; ELSD: gas pressure 40 psi, drift tube temp: 50° C.; column: Waters XSelect CSH C18, 50x2.1 mm, 2.5 μm, Temp: 25° C., Flow: 0.6 mL/min, Gradient: t0=5% B, t2.0 min=98% B, t2.7 min=98% B, Post-time: 0.3 min, Eluent A: 10 mM ammonium bicarbonate in water (pH=9.5), Eluent B: acetonitrile.

Method 4: PREP_ACID-AS3A, Apparatus: Agilent Technologies G6130B Quadrupole; HPLC instrument type: Agilent Technologies 1290 preparative LC; Column: Waters XSelect CSH (C18, 100x30 mm, 10 μ), Flow: 55 ml/min, Column temp: RT; Eluent A: 0.1° /o formic acid in water; Eluent B: 100% acetonitrile; lin. gradient: t=0 min 10% B, t=2 min 10% B, t=8.5 min 50% B, t=10 min 100% B, t=10 min 100% B; Detection: DAD (220-320 nm); Detection: MSD (ESI pos/neg) mass range: 100-1000; fraction collection based on MS and DAD.

Method 5: PREP_ACID-AS4A, Apparatus: Agilent Technologies G6130B Quadrupole; HPLC instrument type: Agilent Technologies 1290 preparative LC; Column: Waters XSelect CSH (C18, 100x30 mm, 10 μ), Flow: 55 ml/min, Column temp: RT; Eluent A: 0.1% formic acid in water; Eluent B: 100% acetonitrile lin. gradient: t=0 min 20% B, t=2 min 20% B, t=8.5 min 60% B, t=10 min 100% B, t=13 min 100% B; Detection: DAD (220-320 nm); Detection: MSD (ESI pos/neg) mass range: 100-1000; fraction collection based on MS and DAD.

$^1H$ NMR

1H-NMR spectra were recorded at 400 MHz on a Bruker Avance AV-I-400 instrument or on a Bruker Avance AV-II-400 instrument. Chemical shift values are expressed in ppm-values relative to tetramethylsilane unless noted otherwise. The following abbreviations or their combinations are used for multiplicity of NMR signals: br=broad, d=doublet, m=multiplet, q=quartet, quint=quintet, s=singlet and t=triplet.

BIOLOGICAL DATA

Neurotensin Scintillation Proximity Assay

The exemplified compounds of the invention were tested in a Neurotensin (NTS) scintillation proximity assay (SPA) and the $IC_{50}$ data is shown in Table 2 below. NTS, which is a 13 amino acid neuropeptide, is a sortilin ligand. The $IC_{50}$ is a measure of the amount of the compound required to inhibit the binding of NTS to sortilin by 50%. The skilled person will recognise that the lower the $IC_{50}$ value, the less of the compound needed to achieve the desired effect, and as a result, the chances of undesirable off-target effects are reduced.

Human Sortilin Binding Assay

The compound affinity was determined by measuring the inhibition of $^3H$-neurotensin and/or $^{125}I$-neurotensin binding to human full length sortilin using a Scintillation Proximity Assay (SPA) format.

The human sortilin SPA binding assay was performed in a total volume of 40 μl in 50 mM HEPES pH 7.4 assay buffer containing 100 mM NaCl, 2.0 mM $CaCl_2$, 0.1% (v:v) BSA and 0.1% (v:v)Tween-20. Varying concentration of test compounds where pre-incubated for 30 min at RT with 150 nM of c-terminal hexahistidine- human full length Sortilin (RD Systems). 5 nM [$^3H$]-Neurotensin or 0.35 nM [$^{125}I$]-Neurotensin was added as radioligand and nonspecific binding defined as the binding observed in the presence 20 μM of human Neurotensin. 0.1 mg PVT copper HIS-tag imaging beads (Perkin Elmer) was added and the plate was agitated at 400 rpm in the dark for 1 hr. The SPA beads were allowed a minimum 2 hours settling time before the plate was read on a Hidex Sense 425-301 scintillation reader with a 45 sec exposure time. Concentration-response evaluation of test compounds was performed with 8 different concentrations of compound (covering 3 decades). Using assay high and low controls (0 μM and 20 μM human neurotensin, respectively), relative $IC_{50}$ values were calculated by nonlinear regression analysis using the sigmoid concentration-response (variable slope) fitting option available in GraphPad Prism 9.0. The compound potency results were converted to inhibition constant Ki values (nM) derived from calculated $IC_{50}$ values converted to Ki values using the Cheng-Prusoff equation (Ki=IC50/(I+(L/Kd))). Kd for human neurotensin was experimentally determined by saturation binding as 374 nM (n=2).

TABLE 2

| Example Number | hSortilin NTS Binding $IC_{50}$ (nM) [3H] neurotensin | hSortilin NTS binding $IC_{50}$ (nM) [125I] neurotensin | hSortilin Ki |
|---|---|---|---|
| 2 | 60 | 105 | |
| 3 | 340 | | 340 |
| 24 | 725 | | |

REFERENCES

1. Tauris, J., et al., Proneurotrophin-3 May Induce Sortilin-Dependent Death In Inner Ear Neurons. *Eur J Neuroscience* (2020), 33(4), pp.622-31.
2. Goettsch, C., et al., Sortilin and Its Multiple Roles in Cardiovascular and Metabolic Diseases. *Atherosclerosis, Thrombosis and Vascular Biology* (2017), 38(1), pp. 19-25.
3. Willnow, T. E., et al., Sortilins: new players in lipoprotein metabolism. *Current Opinion in Lipidology* (2011), 22(2), pp. 79-85.
4. Kjolby, M., et al., Sort1, encoded by the cardiovascular risk locus 1p13.3, is a regulator of hepatic lipoprotein export. *Cell Metabolism* (2010), 12(3), pp. 213-223.
5. Jansen, P., et al., Roles for the pro-neurotrophin receptor sortilin in neuronal development, aging and brain injury. *Nature Neuroscience* (2007), 10(11), pp.1449-1457.
6. Tenk, H. K., et al., ProBDNF induces neuronal apoptosis via activation of a receptor complex of p75NTR and sortilin. *J Neuroscience* (2005), 10(11), pp.1449-1457.
7. Nykjaer, A., et al., Sortilin is essential for proNGF-induced neuronal cell death. *Nature* (2004), 427(6977), pp.843-848.

```
Sequences referenced throughout the
specification and forming part of the
description.
(full length sortilin-isoform 1)
                                SEQ ID NO: 1
        1 MERPWGAADG LSRWPHGLGL LLLLQLLPPS

          TLSQDRLDAP PPPAAPLPRW

       51 SGPIGVSWGL RAAAAGGAFP RGGRWRRSAP

          GEDEECGRVR DFVAKLANNT

      101 HQHVFDDLRG SVSLSWVGDS TGVILVLTTF

          HVPLVIMTFG QSKLYRSEDY

      151 GKNFKDITDL INNTFIRTEF GMAIGPENSG

          KVVLTAEVSG GSRGGRIFRS

      201 SDFAKNFVQT DLPFHPLTQM MYSPQNSDYL

          LALSTENGLW VSKNFGGKWE

      251 EIHKAVCLAK WGSDNTIFFT TYANGSCKAD

          LGALELWRTS DLGKSFKTIG

      301 VKIYSFGLGG RFLFASVMAD KDTTRRIHVS

          TDQGDTWSMA QLPSVGQEQF

      351 YSILAANDDM VFMHVDEPGD TGFGTIFTSD

          DRGIVYSKSL DRHLYTTTGG

      401 ETDFTNVTSL RGVYITSVLS EDNSIQTMIT
```

-continued

FDQGGRWTHL RKPENSECDA

451 TAKNKNECSL HIHASYSISQ KLNVPMAPLS

EPNAVGIVIA HGSVGDAISV

501 MVPDVYISDD GGYSWTKMLE GPHYYTILDS

GGIIVAIEHS SRPINVIKFS

551 TDEGQCWQTY TFTRDPIYFT GLASEPGARS

MNISIWGFTE SFLTSQWVSY

601 TIDFKDILER NCEEKDYTIW LAHSTDPEDY

EDGCILGYKE QFLRLRKSSM

651 CQNGRDYVVT KQPSICLCSL EDFLCDFGYY

RPENDSKCVE QPELKGHDLE

701 FCLYGREEHL TTNGYRKIPG DKCQGGVNPV

REVKDLKKKC TSNFLSPEKQ

751 NSKSNSVPII LAIVGLMLVT VVAGVLIVKK

YVCGGRFLVH RYSVLQQHAE

801 ANGVDGVDAL DTASHTNKSG YHDDSDEDLL

E (full length sortilin-isoform 2)

SEQ ID NO: 2

1 MERPWGAADG LSRWPHGLGL LLLLQLLPPS

TLSQDRLDAP PPPAAPLPRW

51 SGPIGVSWGL RAAAAGGAFP RGGRWRRSAP

GEDEECGRVR DFVAKLANNT

101 HQHVFDDLRG SVSLSWVGDS TGVILVLTTF

HVPLVIMTFG QSKLYRSEDY

151 GKNFKDITDL INNTFIRTEF GMAIGPENSG

KVVLTAEVSG GSRGGRIFRS

201 SDFAKNFVQT DLPFHPLTQM MYSPQNSDYL

LALSTENGLW VSKNFGGKWE

251 EIHKAVCLAK WGSDNTIFFT TYANGSCTDL

GALELWRTSD LGKSFKTIGV

301 KIYSFGLGGR FLFASVMADK DTTRRIHVST

DQGDTWSMAQ LPSVGQEQFY

351 SILAANDDMV FMHVDEPGDT GFGTIFTSDD

RGIVYSKSLD RHLYTTTGGE

401 TDFTNVTSLR GVYITSVLSE DNSIQTMITF

DQGGRWTHLR KPENSECDAT

451 AKNKNECSLH IHASYSISQK LNVPMAPLSE

PNAVGIVIAH GSVGDAISVM

501 VPDVYISDDG GYSWTKMLEG PHYYTILDSG

GIIVAIEHSS RPINVIKFST

-continued

551 DEGQCWQTYT FTRDPIYFTG LASEPGARSM

NISIWGFTES FLTSQWVSYT

601 IDFKDILERN CEEKDYTIWL AHSTDPEDYE

DGCILGYKEQ FLRLRKSSVC

651 QNGRDYVVTK QPSICLCSLE DFLCDFGYYR

PENDSKCVEQ PELKGHDLEF

701 CLYGREEHLT TNGYRKIPGD KCQGGVNPVR

EVKDLKKKCT SNFLSPEKQN

751 SKSNSVPIIL AIVGLMLVTV VAGVLIVKKY

VCGGRFLVHR YSVLQQHAEA

801 NGVDGVDALD TASHTNKSGY HDDSDEDLLE (mature sortilin)

SEQ ID NO: 3

1 MTFGQSKLYR SEDYGKNFKD ITDLINNTFI

RTEFGMAIGP ENSGKVVLTA

51 EVSGGSRGGR IFRSSDFAKN FVQTDLPFHP

LTQMMYSPQN SDYLLALSTE

101 NGLWVSKNFG GKWEEIHKAV CLAKWGSDNT

IFFTTYANGS CTDLGALELW

151 RTSDLGKSFK TIGVKIYSFG LGGRFLFASV

MADKDTTRRI HVSTDQGDTW

201 SMAQLPSVGQ EQFYSILAAN DDMVFMHVDE

PGDTGFGTIF TSDDRGIVYS

251 KSLDRHLYTT TGGETDFTNV TSLRGVYITS

VLSEDNSIQT MITFDQGGRW

301 THLRKPENSE CDATAKNKNE CSLHIHASYS

ISQKLNVPMA PLSEPNAVGI

351 VIAHGSVGDA ISVMVPDVYI SDDGGYSWTK

MLEGPHYYTI LDSGGIIVAI

401 EHSSRPINVI KFSTDEGQCW QTYTFTRDPI

YFTGLASEPG ARSMNISIWG

451 FTESFLTSQW VSYTIDFKDI LERNCEEKDY

TIWLAHSTDP EDYEDGCILG

501 YKEQFLRLRK SSVCQNGRDY VVTKQPSICL

CSLEDFLCDF GYYRPENDSK

551 CVEQPELKGH DLEFCLYGRE EHLTTNGYRK

IPGDKCQGGV NPVREVKDLK

601 KKCTSNFLSP EKQNSKSNSV PIILAIVGLM

LVTVVAGVLI VKKYVCGGRF

651 LVHRYSVLQQ HAEANGVDGV DALDTASHTN

KSGYHDDSDE DLLE

The invention claimed is:

1. A compound of formula (I)

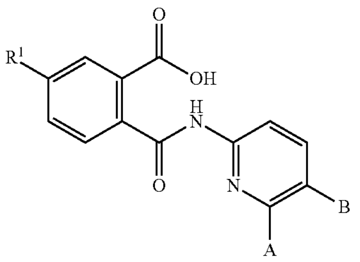

(I)

or a pharmaceutically acceptable salt, solvate, hydrate, tautomer, optical isomer, N-oxide, and/or prodrug thereof, wherein A and B are taken together with the carbon atom to which they are respectively attached to form a 5- to 7-membered monocyclic heterocyclic ring that is optionally substituted with one or more substituents independently selected from —OH, $C_1$-$C_4$ alkyl, $C_1$-$C_4$ haloalkyl and $C_1$-$C_4$ alkoxy and $C_1$-$C_4$ haloalkoxy; and $R^1$ is selected from the group consisting of halo, $C_1$-$C_6$ alkyl, $C_2$-$C_6$ alkenyl, halo $C_1$-$C_6$ alkyl, and halo $C_2$-$C_6$ alkenyl.

2. The compound according to claim 1, wherein $R^1$ is selected from the group consisting of halo, $C_1$-$C_4$ alkyl and halo $C_1$-$C_4$ alkyl, preferably fluoro $C_1$-$C_4$ alkyl.

3. The compound according to claim 1, wherein $R^1$ is selected from the group consisting of $CF_3$ and t-butyl.

4. The compound according to claim 1, wherein A and B are taken together with the carbon atom to which they are respectively attached to form a 6-membered monocyclic heterocyclic ring that is optionally substituted with one or more substituents independently selected from $C_1$-$C_4$ alkyl and $C_1$-$C_4$ haloalkyl, preferably the 6-membered monocyclic heterocyclic ring is unsubstituted.

5. The compound according to claim 4, wherein the 6-membered monocyclic heterocyclic ring comprises an oxygen atom.

6. The compound according to claim 1, wherein the compound of Formula (I) is 2-({5H,6H,8H-pyrano[3,4-b]pyridin-2-yl}carbamoyl)-5-(trifluoromethyl)benzoic acid;

2-({2H,3H,4H-pyrano[2,3-b]pyridin-7-yl}carbamoyl)-5-(trifluoromethyl)benzoic acid;

2-({2H,3H-[1,4]dioxino[2,3-b]pyridin-6-yl}carbamoyl)-5-(trifluoromethyl)benzoic acid;

2-({5H,7H,8H-pyrano[4,3-b]pyridin-2-yl}carbamoyl)-5-(trifluoromethyl)benzoic acid;

2-[(5,6,7,8-tetrahydro-1,6-naphthyridin-2-yl)carbamoyl]-5-(trifluoromethyl)benzoic acid;

5-tert-butyl-2-({5H,6H,8H-pyrano[3,4-b]pyridin-2-yl}carbamoyl)benzoic acid;

or a pharmaceutically acceptable salt, solvate, hydrate, tautomer, optical isomer, N-oxide, and/or prodrug thereof.

7. A pharmaceutical composition comprising a compound according to claim 1 and a pharmaceutically acceptable carrier, excipient, and/or diluent.

8. A method of treating a disorder or disease, a comprising administering the pharmaceutical composition of claim 7 to a subject, wherein the disorder or disease is:

a neurodegenerative disorder selected from frontotemporal dementia, Alzheimer's disease, Parkinson's disease and spinal cord injury;

a cancer is selected from breast cancer, lung cancer, ovarian cancer, prostate cancer, thyroid cancer, pancreatic cancer, glioblastoma and colorectal cancer;

diabetes mellitus;

diabetic retinopathy; or hearing loss selected from noise-induced hearing loss, ototoxicity induced hearing loss, age-induced hearing loss, idiopathic hearing loss, tinnitus and sudden hearing loss.

9. The compound of claim 2, wherein $R_1$ is fluoro $C_1$-$C_4$ alkyl.

10. The compound of claim 4, wherein A and B are taken together with the carbon atom to which they are respectively attached to form a 6-membered monocyclic heterocyclic ring that is unsubstituted.

* * * * *

SEQUENCE LISTING

<160> NUMBER OF SEQ ID NOS: 3

<210> SEQ ID NO 1
<211> LENGTH: 831
<212> TYPE: PRT
<213> ORGANISM: Homo sapiens

<400> SEQUENCE: 1

Met Glu Arg Pro Trp Gly Ala Ala Asp Gly Leu Ser Arg Trp Pro His
1               5                   10                  15

Gly Leu Gly Leu Leu Leu Leu Leu Gln Leu Leu Pro Pro Ser Thr Leu
            20                  25                  30

Ser Gln Asp Arg Leu Asp Ala Pro Pro Pro Pro Ala Ala Pro Leu Pro
        35                  40                  45

Arg Trp Ser Gly Pro Ile Gly Val Ser Trp Gly Leu Arg Ala Ala Ala
    50                  55                  60

Ala Gly Gly Ala Phe Pro Arg Gly Gly Arg Trp Arg Arg Ser Ala Pro
65                  70                  75                  80

Gly Glu Asp Glu Glu Cys Gly Arg Val Arg Asp Phe Val Ala Lys Leu
                85                  90                  95

Ala Asn Asn Thr His Gln His Val Phe Asp Asp Leu Arg Gly Ser Val
            100                 105                 110

Ser Leu Ser Trp Val Gly Asp Ser Thr Gly Val Ile Leu Val Leu Thr
        115                 120                 125

Thr Phe His Val Pro Leu Val Ile Met Thr Phe Gly Gln Ser Lys Leu
    130                 135                 140

Tyr Arg Ser Glu Asp Tyr Gly Lys Asn Phe Lys Asp Ile Thr Asp Leu
145                 150                 155                 160

Ile Asn Asn Thr Phe Ile Arg Thr Glu Phe Gly Met Ala Ile Gly Pro
                165                 170                 175

Glu Asn Ser Gly Lys Val Val Leu Thr Ala Glu Val Ser Gly Gly Ser
            180                 185                 190

Arg Gly Gly Arg Ile Phe Arg Ser Ser Asp Phe Ala Lys Asn Phe Val
        195                 200                 205

Gln Thr Asp Leu Pro Phe His Pro Leu Thr Gln Met Met Tyr Ser Pro
    210                 215                 220

Gln Asn Ser Asp Tyr Leu Leu Ala Leu Ser Thr Glu Asn Gly Leu Trp
225                 230                 235                 240

Val Ser Lys Asn Phe Gly Gly Lys Trp Glu Glu Ile His Lys Ala Val
                245                 250                 255

Cys Leu Ala Lys Trp Gly Ser Asp Asn Thr Ile Phe Phe Thr Thr Tyr
            260                 265                 270

Ala Asn Gly Ser Cys Lys Ala Asp Leu Gly Ala Leu Glu Leu Trp Arg
        275                 280                 285

Thr Ser Asp Leu Gly Lys Ser Phe Lys Thr Ile Gly Val Lys Ile Tyr
    290                 295                 300

Ser Phe Gly Leu Gly Gly Arg Phe Leu Phe Ala Ser Val Met Ala Asp
305                 310                 315                 320

Lys Asp Thr Thr Arg Arg Ile His Val Ser Thr Asp Gln Gly Asp Thr
                325                 330                 335

Trp Ser Met Ala Gln Leu Pro Ser Val Gly Gln Glu Gln Phe Tyr Ser
            340                 345                 350

Ile Leu Ala Ala Asn Asp Asp Met Val Phe Met His Val Asp Glu Pro
        355                 360                 365

-continued

```
Gly Asp Thr Gly Phe Gly Thr Ile Phe Thr Ser Asp Asp Arg Gly Ile
    370                 375                 380

Val Tyr Ser Lys Ser Leu Asp Arg His Leu Tyr Thr Thr Thr Gly Gly
385                 390                 395                 400

Glu Thr Asp Phe Thr Asn Val Thr Ser Leu Arg Gly Val Tyr Ile Thr
                405                 410                 415

Ser Val Leu Ser Glu Asp Asn Ser Ile Gln Thr Met Ile Thr Phe Asp
            420                 425                 430

Gln Gly Gly Arg Trp Thr His Leu Arg Lys Pro Glu Asn Ser Glu Cys
        435                 440                 445

Asp Ala Thr Ala Lys Asn Lys Asn Glu Cys Ser Leu His Ile His Ala
    450                 455                 460

Ser Tyr Ser Ile Ser Gln Lys Leu Asn Val Pro Met Ala Pro Leu Ser
465                 470                 475                 480

Glu Pro Asn Ala Val Gly Ile Val Ile Ala His Gly Ser Val Gly Asp
                485                 490                 495

Ala Ile Ser Val Met Val Pro Asp Val Tyr Ile Ser Asp Asp Gly Gly
            500                 505                 510

Tyr Ser Trp Thr Lys Met Leu Glu Gly Pro His Tyr Tyr Thr Ile Leu
        515                 520                 525

Asp Ser Gly Gly Ile Ile Val Ala Ile Glu His Ser Ser Arg Pro Ile
    530                 535                 540

Asn Val Ile Lys Phe Ser Thr Asp Glu Gly Gln Cys Trp Gln Thr Tyr
545                 550                 555                 560

Thr Phe Thr Arg Asp Pro Ile Tyr Phe Thr Gly Leu Ala Ser Glu Pro
                565                 570                 575

Gly Ala Arg Ser Met Asn Ile Ser Ile Trp Gly Phe Thr Glu Ser Phe
            580                 585                 590

Leu Thr Ser Gln Trp Val Ser Tyr Thr Ile Asp Phe Lys Asp Ile Leu
        595                 600                 605

Glu Arg Asn Cys Glu Glu Lys Asp Tyr Thr Ile Trp Leu Ala His Ser
    610                 615                 620

Thr Asp Pro Glu Asp Tyr Glu Asp Gly Cys Ile Leu Gly Tyr Lys Glu
625                 630                 635                 640

Gln Phe Leu Arg Leu Arg Lys Ser Ser Met Cys Gln Asn Gly Arg Asp
                645                 650                 655

Tyr Val Val Thr Lys Gln Pro Ser Ile Cys Leu Cys Ser Leu Glu Asp
            660                 665                 670

Phe Leu Cys Asp Phe Gly Tyr Tyr Arg Pro Glu Asn Asp Ser Lys Cys
        675                 680                 685

Val Glu Gln Pro Glu Leu Lys Gly His Asp Leu Glu Phe Cys Leu Tyr
    690                 695                 700

Gly Arg Glu Glu His Leu Thr Thr Asn Gly Tyr Arg Lys Ile Pro Gly
705                 710                 715                 720

Asp Lys Cys Gln Gly Gly Val Asn Pro Val Arg Glu Val Lys Asp Leu
                725                 730                 735

Lys Lys Lys Cys Thr Ser Asn Phe Leu Ser Pro Glu Lys Gln Asn Ser
            740                 745                 750

Lys Ser Asn Ser Val Pro Ile Ile Leu Ala Ile Val Gly Leu Met Leu
        755                 760                 765

Val Thr Val Val Ala Gly Val Leu Ile Val Lys Lys Tyr Val Cys Gly
    770                 775                 780

Gly Arg Phe Leu Val His Arg Tyr Ser Val Leu Gln Gln His Ala Glu
```

-continued

```
785                 790                 795                 800

Ala Asn Gly Val Asp Gly Val Asp Ala Leu Asp Thr Ala Ser His Thr
                805                 810                 815

Asn Lys Ser Gly Tyr His Asp Asp Ser Asp Glu Asp Leu Leu Glu
            820                 825                 830


<210> SEQ ID NO 2
<211> LENGTH: 830
<212> TYPE: PRT
<213> ORGANISM: Homo sapiens

<400> SEQUENCE: 2

Met Glu Arg Pro Trp Gly Ala Ala Asp Gly Leu Ser Arg Trp Pro His
1               5                   10                  15

Gly Leu Gly Leu Leu Leu Leu Leu Gln Leu Leu Pro Pro Ser Thr Leu
            20                  25                  30

Ser Gln Asp Arg Leu Asp Ala Pro Pro Pro Ala Ala Pro Leu Pro
        35                  40                  45

Arg Trp Ser Gly Pro Ile Gly Val Ser Trp Gly Leu Arg Ala Ala Ala
    50                  55                  60

Ala Gly Gly Ala Phe Pro Arg Gly Gly Arg Trp Arg Arg Ser Ala Pro
65                  70                  75                  80

Gly Glu Asp Glu Glu Cys Gly Arg Val Arg Asp Phe Val Ala Lys Leu
                85                  90                  95

Ala Asn Asn Thr His Gln His Val Phe Asp Asp Leu Arg Gly Ser Val
            100                 105                 110

Ser Leu Ser Trp Val Gly Asp Ser Thr Gly Val Ile Leu Val Leu Thr
        115                 120                 125

Thr Phe His Val Pro Leu Val Ile Met Thr Phe Gly Gln Ser Lys Leu
    130                 135                 140

Tyr Arg Ser Glu Asp Tyr Gly Lys Asn Phe Lys Asp Ile Thr Asp Leu
145                 150                 155                 160

Ile Asn Asn Thr Phe Ile Arg Thr Glu Phe Gly Met Ala Ile Gly Pro
                165                 170                 175

Glu Asn Ser Gly Lys Val Val Leu Thr Ala Glu Val Ser Gly Gly Ser
            180                 185                 190

Arg Gly Gly Arg Ile Phe Arg Ser Ser Asp Phe Ala Lys Asn Phe Val
        195                 200                 205

Gln Thr Asp Leu Pro Phe His Pro Leu Thr Gln Met Met Tyr Ser Pro
    210                 215                 220

Gln Asn Ser Asp Tyr Leu Leu Ala Leu Ser Thr Glu Asn Gly Leu Trp
225                 230                 235                 240

Val Ser Lys Asn Phe Gly Gly Lys Trp Glu Glu Ile His Lys Ala Val
                245                 250                 255

Cys Leu Ala Lys Trp Gly Ser Asp Asn Thr Ile Phe Phe Thr Thr Tyr
            260                 265                 270

Ala Asn Gly Ser Cys Thr Asp Leu Gly Ala Leu Glu Leu Trp Arg Thr
        275                 280                 285

Ser Asp Leu Gly Lys Ser Phe Lys Thr Ile Gly Val Lys Ile Tyr Ser
    290                 295                 300

Phe Gly Leu Gly Gly Arg Phe Leu Phe Ala Ser Val Met Ala Asp Lys
305                 310                 315                 320

Asp Thr Thr Arg Arg Ile His Val Ser Thr Asp Gln Gly Asp Thr Trp
                325                 330                 335
```

-continued

```
Ser Met Ala Gln Leu Pro Ser Val Gly Gln Glu Gln Phe Tyr Ser Ile
            340                 345                 350

Leu Ala Ala Asn Asp Asp Met Val Phe Met His Val Asp Glu Pro Gly
        355                 360                 365

Asp Thr Gly Phe Gly Thr Ile Phe Thr Ser Asp Asp Arg Gly Ile Val
    370                 375                 380

Tyr Ser Lys Ser Leu Asp Arg His Leu Tyr Thr Thr Thr Gly Gly Glu
385                 390                 395                 400

Thr Asp Phe Thr Asn Val Thr Ser Leu Arg Gly Val Tyr Ile Thr Ser
                405                 410                 415

Val Leu Ser Glu Asp Asn Ser Ile Gln Thr Met Ile Thr Phe Asp Gln
            420                 425                 430

Gly Gly Arg Trp Thr His Leu Arg Lys Pro Glu Asn Ser Glu Cys Asp
        435                 440                 445

Ala Thr Ala Lys Asn Lys Asn Glu Cys Ser Leu His Ile His Ala Ser
    450                 455                 460

Tyr Ser Ile Ser Gln Lys Leu Asn Val Pro Met Ala Pro Leu Ser Glu
465                 470                 475                 480

Pro Asn Ala Val Gly Ile Val Ile Ala His Gly Ser Val Gly Asp Ala
                485                 490                 495

Ile Ser Val Met Val Pro Asp Val Tyr Ile Ser Asp Asp Gly Gly Tyr
            500                 505                 510

Ser Trp Thr Lys Met Leu Glu Gly Pro His Tyr Tyr Thr Ile Leu Asp
        515                 520                 525

Ser Gly Gly Ile Ile Val Ala Ile Glu His Ser Ser Arg Pro Ile Asn
    530                 535                 540

Val Ile Lys Phe Ser Thr Asp Glu Gly Gln Cys Trp Gln Thr Tyr Thr
545                 550                 555                 560

Phe Thr Arg Asp Pro Ile Tyr Phe Thr Gly Leu Ala Ser Glu Pro Gly
                565                 570                 575

Ala Arg Ser Met Asn Ile Ser Ile Trp Gly Phe Thr Glu Ser Phe Leu
            580                 585                 590

Thr Ser Gln Trp Val Ser Tyr Thr Ile Asp Phe Lys Asp Ile Leu Glu
        595                 600                 605

Arg Asn Cys Glu Glu Lys Asp Tyr Thr Ile Trp Leu Ala His Ser Thr
    610                 615                 620

Asp Pro Glu Asp Tyr Glu Asp Gly Cys Ile Leu Gly Tyr Lys Glu Gln
625                 630                 635                 640

Phe Leu Arg Leu Arg Lys Ser Ser Val Cys Gln Asn Gly Arg Asp Tyr
                645                 650                 655

Val Val Thr Lys Gln Pro Ser Ile Cys Leu Cys Ser Leu Glu Asp Phe
            660                 665                 670

Leu Cys Asp Phe Gly Tyr Tyr Arg Pro Glu Asn Asp Ser Lys Cys Val
        675                 680                 685

Glu Gln Pro Glu Leu Lys Gly His Asp Leu Glu Phe Cys Leu Tyr Gly
    690                 695                 700

Arg Glu Glu His Leu Thr Thr Asn Gly Tyr Arg Lys Ile Pro Gly Asp
705                 710                 715                 720

Lys Cys Gln Gly Gly Val Asn Pro Val Arg Glu Val Lys Asp Leu Lys
                725                 730                 735

Lys Lys Cys Thr Ser Asn Phe Leu Ser Pro Glu Lys Gln Asn Ser Lys
            740                 745                 750

Ser Asn Ser Val Pro Ile Ile Leu Ala Ile Val Gly Leu Met Leu Val
```

```
        755                 760                 765

Thr Val Val Ala Gly Val Leu Ile Val Lys Lys Tyr Val Cys Gly Gly
    770                 775                 780

Arg Phe Leu Val His Arg Tyr Ser Val Leu Gln Gln His Ala Glu Ala
785                 790                 795                 800

Asn Gly Val Asp Gly Val Asp Ala Leu Asp Thr Ala Ser His Thr Asn
                805                 810                 815

Lys Ser Gly Tyr His Asp Asp Ser Asp Glu Asp Leu Leu Glu
            820                 825                 830


<210> SEQ ID NO 3
<211> LENGTH: 694
<212> TYPE: PRT
<213> ORGANISM: Homo sapiens

<400> SEQUENCE: 3

Met Thr Phe Gly Gln Ser Lys Leu Tyr Arg Ser Glu Asp Tyr Gly Lys
1               5                   10                  15

Asn Phe Lys Asp Ile Thr Asp Leu Ile Asn Asn Thr Phe Ile Arg Thr
            20                  25                  30

Glu Phe Gly Met Ala Ile Gly Pro Glu Asn Ser Gly Lys Val Val Leu
        35                  40                  45

Thr Ala Glu Val Ser Gly Gly Ser Arg Gly Gly Arg Ile Phe Arg Ser
    50                  55                  60

Ser Asp Phe Ala Lys Asn Phe Val Gln Thr Asp Leu Pro Phe His Pro
65                  70                  75                  80

Leu Thr Gln Met Met Tyr Ser Pro Gln Asn Ser Asp Tyr Leu Leu Ala
                85                  90                  95

Leu Ser Thr Glu Asn Gly Leu Trp Val Ser Lys Asn Phe Gly Gly Lys
            100                 105                 110

Trp Glu Glu Ile His Lys Ala Val Cys Leu Ala Lys Trp Gly Ser Asp
        115                 120                 125

Asn Thr Ile Phe Phe Thr Thr Tyr Ala Asn Gly Ser Cys Thr Asp Leu
    130                 135                 140

Gly Ala Leu Glu Leu Trp Arg Thr Ser Asp Leu Gly Lys Ser Phe Lys
145                 150                 155                 160

Thr Ile Gly Val Lys Ile Tyr Ser Phe Gly Leu Gly Gly Arg Phe Leu
                165                 170                 175

Phe Ala Ser Val Met Ala Asp Lys Asp Thr Thr Arg Arg Ile His Val
            180                 185                 190

Ser Thr Asp Gln Gly Asp Thr Trp Ser Met Ala Gln Leu Pro Ser Val
        195                 200                 205

Gly Gln Glu Gln Phe Tyr Ser Ile Leu Ala Ala Asn Asp Asp Met Val
    210                 215                 220

Phe Met His Val Asp Glu Pro Gly Asp Thr Gly Phe Gly Thr Ile Phe
225                 230                 235                 240

Thr Ser Asp Asp Arg Gly Ile Val Tyr Ser Lys Ser Leu Asp Arg His
                245                 250                 255

Leu Tyr Thr Thr Thr Gly Gly Glu Thr Asp Phe Thr Asn Val Thr Ser
            260                 265                 270

Leu Arg Gly Val Tyr Ile Thr Ser Val Leu Ser Glu Asp Asn Ser Ile
        275                 280                 285

Gln Thr Met Ile Thr Phe Asp Gln Gly Gly Arg Trp Thr His Leu Arg
    290                 295                 300
```

-continued

```
Lys Pro Glu Asn Ser Glu Cys Asp Ala Thr Ala Lys Asn Lys Asn Glu
305                 310                 315                 320

Cys Ser Leu His Ile His Ala Ser Tyr Ser Ile Ser Gln Lys Leu Asn
                325                 330                 335

Val Pro Met Ala Pro Leu Ser Glu Pro Asn Ala Val Gly Ile Val Ile
            340                 345                 350

Ala His Gly Ser Val Gly Asp Ala Ile Ser Val Met Val Pro Asp Val
        355                 360                 365

Tyr Ile Ser Asp Asp Gly Gly Tyr Ser Trp Thr Lys Met Leu Glu Gly
    370                 375                 380

Pro His Tyr Tyr Thr Ile Leu Asp Ser Gly Gly Ile Ile Val Ala Ile
385                 390                 395                 400

Glu His Ser Ser Arg Pro Ile Asn Val Ile Lys Phe Ser Thr Asp Glu
                405                 410                 415

Gly Gln Cys Trp Gln Thr Tyr Thr Phe Thr Arg Asp Pro Ile Tyr Phe
            420                 425                 430

Thr Gly Leu Ala Ser Glu Pro Gly Ala Arg Ser Met Asn Ile Ser Ile
        435                 440                 445

Trp Gly Phe Thr Glu Ser Phe Leu Thr Ser Gln Trp Val Ser Tyr Thr
    450                 455                 460

Ile Asp Phe Lys Asp Ile Leu Glu Arg Asn Cys Glu Glu Lys Asp Tyr
465                 470                 475                 480

Thr Ile Trp Leu Ala His Ser Thr Asp Pro Glu Asp Tyr Glu Asp Gly
                485                 490                 495

Cys Ile Leu Gly Tyr Lys Glu Gln Phe Leu Arg Leu Arg Lys Ser Ser
            500                 505                 510

Val Cys Gln Asn Gly Arg Asp Tyr Val Val Thr Lys Gln Pro Ser Ile
        515                 520                 525

Cys Leu Cys Ser Leu Glu Asp Phe Leu Cys Asp Phe Gly Tyr Tyr Arg
    530                 535                 540

Pro Glu Asn Asp Ser Lys Cys Val Glu Gln Pro Glu Leu Lys Gly His
545                 550                 555                 560

Asp Leu Glu Phe Cys Leu Tyr Gly Arg Glu Glu His Leu Thr Thr Asn
                565                 570                 575

Gly Tyr Arg Lys Ile Pro Gly Asp Lys Cys Gln Gly Gly Val Asn Pro
            580                 585                 590

Val Arg Glu Val Lys Asp Leu Lys Lys Lys Cys Thr Ser Asn Phe Leu
        595                 600                 605

Ser Pro Glu Lys Gln Asn Ser Lys Ser Asn Ser Val Pro Ile Ile Leu
    610                 615                 620

Ala Ile Val Gly Leu Met Leu Val Thr Val Val Ala Gly Val Leu Ile
625                 630                 635                 640

Val Lys Lys Tyr Val Cys Gly Gly Arg Phe Leu Val His Arg Tyr Ser
                645                 650                 655

Val Leu Gln Gln His Ala Glu Ala Asn Gly Val Asp Gly Val Asp Ala
            660                 665                 670

Leu Asp Thr Ala Ser His Thr Asn Lys Ser Gly Tyr His Asp Asp Ser
        675                 680                 685

Asp Glu Asp Leu Leu Glu
    690
```